(12) United States Patent
Kozai

(10) Patent No.: US 11,284,862 B2
(45) Date of Patent: Mar. 29, 2022

(54) ULTRASOUND OBSERVATION DEVICE, METHOD OF OPERATING ULTRASOUND OBSERVATION DEVICE, AND COMPUTER READABLE RECORDING MEDIUM

(71) Applicant: OLYMPUS CORPORATION, Tokyo (JP)

(72) Inventor: Shigenori Kozai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 240 days.

(21) Appl. No.: 16/516,343

(22) Filed: Jul. 19, 2019

(65) Prior Publication Data

US 2019/0336106 A1 Nov. 7, 2019

Related U.S. Application Data

(63) Continuation of application No. PCT/JP2018/001208, filed on Jan. 17, 2018.

(30) Foreign Application Priority Data

Jan. 31, 2017 (JP) .............................. JP2017-015929

(51) Int. Cl.
  *A61B 8/12* (2006.01)
  *A61B 8/00* (2006.01)
  (Continued)

(52) U.S. Cl.
  CPC ............ *A61B 8/469* (2013.01); *A61B 8/5207* (2013.01); *A61B 8/5269* (2013.01); *A61B 8/12* (2013.01); *A61B 8/14* (2013.01); *A61B 8/461* (2013.01)

(58) Field of Classification Search
  CPC .. A61B 8/12; A61B 8/14; A61B 8/461; A61B 8/469; A61B 8/5207; A61B 8/5223; A61B 8/5269; G16H 50/30
  See application file for complete search history.

(56) References Cited

U.S. PATENT DOCUMENTS 7,889,250 B2 * 2/2011 Aragaki .................. G06T 5/008 348/254
8,265,419 B2 * 9/2012 Chen ....................... G06T 5/002 382/274

(Continued)

FOREIGN PATENT DOCUMENTS

| JP | 2016-002208 A | 1/2016 |
| JP | 2016-116792 A | 6/2016 |
| WO | WO 2016/103847 A1 | 6/2016 |

OTHER PUBLICATIONS

International Search Report dated Apr. 24, 2018 issued in PCT/JP2018/001208.

*Primary Examiner* — Mark D Remaly
(74) *Attorney, Agent, or Firm* — Scully, Scott, Murphy & Presser, P.C.

(57) ABSTRACT

An ultrasound observation device includes a processor including hardware, wherein the processor is configured to: generate ultrasound image data; set, in a region of interest, a plurality of small regions by dividing the region of interest in accordance with a preset condition; generate a histogram of each of the small regions; calculate a determination value for each of the small regions; determine whether the physical quantity in each of the small regions is uniform; change a determination target small region in accordance with a preset condition when the physical quantity in the determination target small region among the small regions is determined to be not uniform; set the determination target small region as an attenuation rate calculation target region when the physical quantity in the determination target small region is determined to be uniform; and set an attenuation rate of the attenuation rate calculation target region.

20 Claims, 21 Drawing Sheets

(51) Int. Cl.
*A61B 8/08* (2006.01)
*A61B 8/14* (2006.01)

(56) References Cited

U.S. PATENT DOCUMENTS 9,892,497 B2 * 2/2018 Kino .................. G06T 5/40
10,201,329 B2   2/2019 Ichikawa

* cited by examiner

ULTRASOUND OBSERVATION DEVICE, METHOD OF OPERATING ULTRASOUND OBSERVATION DEVICE, AND COMPUTER READABLE RECORDING MEDIUM This application is a continuation of PCT International Application No. PCT/JP2018/001208 filed on Jan. 17, 2018, which designates the United States, incorporated herein by reference, and which claims the benefit of priority from Japanese Patent Application No. 2017-015929, filed on Jan. 31, 2017, incorporated herein by reference.

BACKGROUND

The present disclosure relates to an ultrasound observation device, a method of operating the ultrasound observation device, and a computer readable recording medium.

Ultrasound waves are sometimes applied to observe the property of living tissue or a material as an observation target. Specifically, the observation target is observed by transmitting ultrasound waves to the observation target, generating an ultrasound image based on ultrasound echoes reflected by the observation target, and displaying the generated ultrasound image.

When diagnosis is performed using the ultrasound image, in some cases, a region to be observed in detail (hereinafter, referred to as a region of interest) may be set in the ultrasound image (for example, see Japanese Laid-open Patent Publication No. 2016-2208). The region of interest is subjected to attenuation correction or the like to increase the precision of an image in the region of interest. Japanese Laid-open Patent Publication No. 2016-2208 describes a technique of setting a plurality of evaluation regions in a region of interest, calculating an evaluation value by using a preset physical quantity for each of the evaluation regions, and re-setting the region of interest based on the evaluation values. In Japanese Laid-open Patent Publication No. 2016-2208, the region of interest is re-set by determining the degree of observation accuracy of each of the evaluation regions by comparing the evaluation amount and a threshold, and eliminating the evaluation regions for each of which it is determined that the degree of observation accuracy is low.

SUMMARY

An ultrasound observation device according to one aspect of the present disclosure includes a processor including hardware, wherein the processor is configured to: generate ultrasound image data based on an ultrasound signal received from an ultrasound transducer configured to transmit an ultrasound wave to an observation target and to receive an ultrasound wave reflected from the observation target; set, in a region of interest that is set in an ultrasound image corresponding to the ultrasound image data, a plurality of small regions by dividing the region of interest in accordance with a preset condition; generate a histogram of each of the small regions based on a preset physical quantity; calculate a determination value for each of the small regions based on the histogram, the determination value determining whether the physical quantity in each of the small regions is uniform; determine whether the physical quantity in each of the small regions is uniform based on the determination value and a preset threshold; change a determination target small region in accordance with a preset condition when the physical quantity in the determination target small region among the small regions is determined to be not uniform; set the determination target small region as an attenuation rate calculation target region when the physical quantity in the determination target small region is determined to be uniform; and set an attenuation rate of the attenuation rate calculation target region.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for carrying out the present disclosure (hereinafter, referred to as "embodiments") will be described below with reference to the accompanying drawings.

First Embodiment

Figure 1:
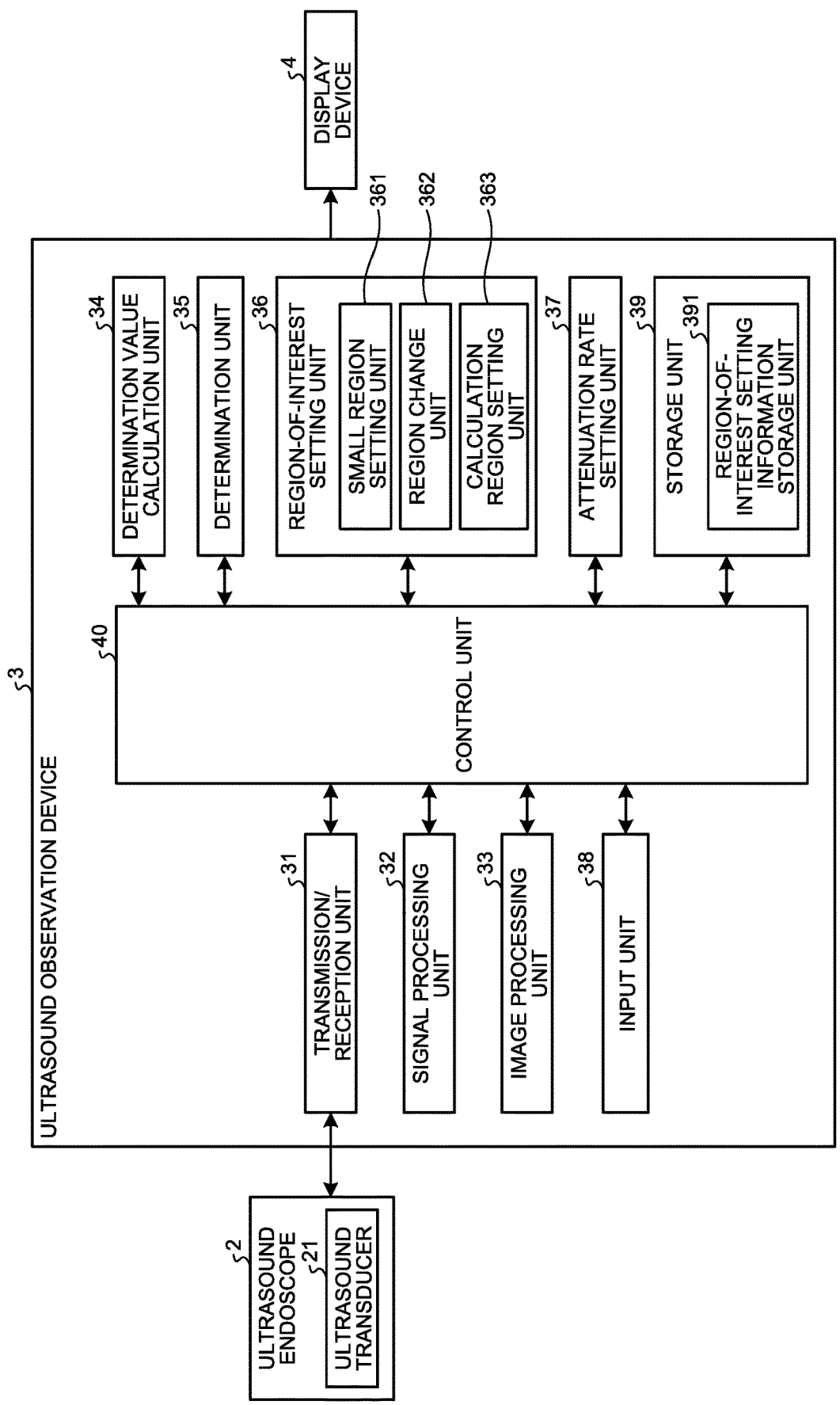
FIG. 1 is a block diagram illustrating a configuration of an ultrasound diagnosis system including an ultrasound observation device according to a first embodiment.

FIG. 1 is a block diagram illustrating a configuration of an ultrasound diagnosis system including an ultrasound observation device according to a first embodiment. An ultrasound diagnosis system 1 illustrated in FIG. 1 includes an ultrasound endoscope 2 that transmits ultrasound waves to a subject as an observation target and receives ultrasound waves reflected by the subject, an ultrasound observation device 3 that generates an ultrasound image based on an ultrasound signal acquired by the ultrasound endoscope 2, and a display device 4 that displays the ultrasound image generated by the ultrasound observation device 3.

The ultrasound endoscope 2 includes, in a distal end portion thereof, an ultrasound transducer 21 that converts an electrical pulse signal received from the ultrasound observation device 3 into an ultrasound pulse (acoustic pulse), applies the ultrasound pulse to the subject, converts an ultrasound echo reflected by the subject into an electrical echo signal (ultrasound signal) that represents the ultrasound echo by a voltage change, and outputs the echo signal. The ultrasound transducer 21 is realized by a radial transducer. The ultrasound endoscope 2 may cause the ultrasound transducer 21 to mechanically perform scanning, or may include, as the ultrasound transducer 21, a plurality of elements in an array manner and cause the ultrasound transducer 21 to electronically perform scanning by electronically switching between the elements involved in transmission and reception or delaying transmission and reception in each of the elements.

The ultrasound endoscope 2 normally includes an imaging optical system and an imaging element, is inserted in a digestive tract (an esophagus, a stomach, a duodenum, or a large intestine) or a respiratory organ (a trachea or a bronchus) of the subject, and is able to capture images of the digestive tract, the respiratory organ, or organs around the digestive tract or the respiratory organ (a pancreas, a gallbladder, a bile duct, a biliary tract, lymph nodes, a mediastinal organ, a blood vessel, or the like). Further, the ultrasound endoscope 2 includes a light guide that guides illumination light to be applied to the subject at the time of imaging. A distal end portion of the light guide reaches a distal end of an insertion portion of the ultrasound endoscope 2 to be inserted in the subject, and a proximal end portion of the light guide is connected to a light source device that emits the illumination light.

The ultrasound observation device 3 includes a transmission/reception unit 31, a signal processing unit 32, an image processing unit 33, a determination value calculation unit 34, a determination unit 35, a region-of-interest setting unit 36, an attenuation rate setting unit 37, an input unit 38, a storage unit 39, and a control unit 40.

The transmission/reception unit 31 is electrically connected to the ultrasound endoscope 2, transmits a transmission signal (pulse signal) with a high voltage pulse to the ultrasound transducer 21 based on a predetermined waveform and a transmission timing, receives an echo signal that is an electrical reception signal from the ultrasound transducer 21, generates data (hereinafter, referred to as RF data) of a digital high-frequency (radio frequency (RF)) signal, and outputs the data.

It is preferable to set a frequency band of the pulse signal transmitted by the transmission/reception unit 31 to a wide band that covers almost the whole linear response frequency band that is used for electroacoustic conversion from the pulse signal to the ultrasound pulse in the ultrasound transducer 21.

The transmission/reception unit 31 also has a function to transmit various control signals output by the control unit 40 to the ultrasound endoscope 2, receive various kinds of information including an ID for identification from the ultrasound endoscope 2, and transmit the received information to the control unit 40.

The signal processing unit 32 generates digital B-mode reception data based on the RF data received from the transmission/reception unit 31. Specifically, the signal processing unit 32 performs known processing, such as bandpass filtering, envelope detection, logarithmic transformation, and attenuation correction, on the RF data, and generates the digital B-mode reception data. In the logarithmic transformation, a common logarithm of the RF data divided by a reference voltage is calculated represented by a decibel value. The B-mode reception data includes a plurality of pieces of line data in which an amplitude or intensity of the reception signal indicating an intensity of reflection of the ultrasound pulse is arranged along a transmission/reception direction (depth direction) of the ultrasound pulse. The signal processing unit 32 outputs the generated B-mode reception data for a single frame to the image processing unit 33. The signal processing unit 32 is realized by using a general-purpose processor, such as a central processing unit (CPU), a dedicated integrated circuit or a custom type processor, such as an application specific integrated circuit (ASIC) or a field programmable gate array (FPGA), which implements a specific function, or the like.

The image processing unit 33 generates B-mode image data based on the B-mode reception data received from the signal processing unit 32. The image processing unit 33 performs signal processing using a known technique, such as scan conversion processing, gain processing, or contrast processing, on the B-mode reception data output from the signal processing unit 32, and generates the B-mode image data by performing data thinning or the like in accordance with a data step width that is defined by an image display range of the display device 4. In the scan conversion processing, a scanning direction of the B-mode reception data is converted from an ultrasound wave scanning direction to a display direction of the display device 4. The B-mode image is a grayscale image in which R (red), G (green), and B (blue) values are set to the same value, where the RGB values are variables used when the RGB color system is adopted as a color system. Hereinafter, a value that corresponds to each of pixel positions of the B-mode image, that is obtained by adding the RGB values, and that represents brightness at each of the pixel positions is referred to as luminance.

The image processing unit 33 performs, on pieces of B-mode reception data received from the signal processing unit 32, coordinate transformation for rearranging the pieces of B-mode reception data so that a scanning range can be represented in a spatially correct manner, and performs an interpolation process between the pieces of B-mode reception data to fill gaps between the pieces of B-mode reception data, to thereby generate the B-mode image data. The image processing unit 33 is realized by using a general-purpose processor, such as a CPU, a dedicated integrated circuit or a custom type processor, such as an ASIC or an FPGA, which implements a specific function, or the like.

The determination value calculation unit 34 calculates a determination value of a calculation region by using a preset physical quantity. In the first embodiment, luminance is used as the physical quantity, a histogram of luminance with respect to a frequency in a small region, which is set in the region of interest, or in a divided region, which is set by dividing the small region, is generated, and a variation of the histogram is calculated as the determination value. The variation is, for example, standard deviation of luminance. The small region and the divided region will be described later. The determination value calculation unit 34 is realized by using a general-purpose processor, such as a CPU, a dedicated integrated circuit or a custom type processor, such as an ASIC or an FPGA, which implements a specific function, or the like.

The determination unit 35 determines whether luminance in a determination target small region or luminance in a determination target divided region is uniform based on the determination value calculated by the determination value calculation unit 34. Specifically, the determination unit 35 determines whether the determination value exceeds a preset threshold, and determines that the luminance is uniform if the determination value does not exceed the threshold. In contrast, the determination unit 35 determines that the luminance is not uniform if the determination value exceeds the threshold. The determination unit 35 is realized by using a general-purpose processor, such as a CPU, a dedicated integrated circuit or a custom type processor, such as an ASIC or an FPGA, which implements a specific function, or the like.

Figure 2:
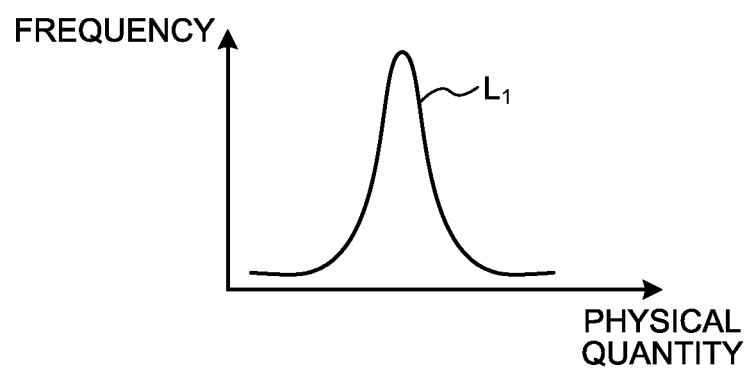
FIG. 2 is a diagram illustrating a frequency distribution in a case where a physical quantity is uniform.

FIG. 2 is a diagram illustrating a frequency distribution in a case where the physical quantity is uniform. If the luminance in the region is represented by a frequency distribution with a small variation like a distribution curve $L_1$ as illustrated in FIG. 2 and if a standard deviation that is the determination value is small, the determination unit 35 determines that the luminance in the region is uniform.

Figure 3:
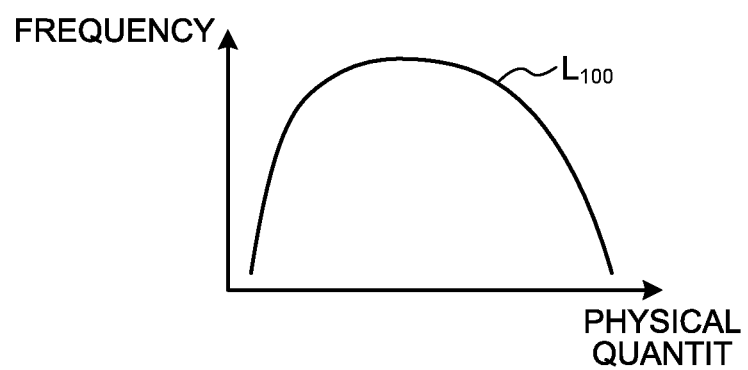
FIG. 3 is a diagram illustrating a frequency distribution in a case where the physical quantity is not uniform.

FIG. 3 is a diagram illustrating a frequency distribution in a case where the physical quantity is not uniform. As compared to the frequency distribution illustrated in FIG. 2, if the luminance in the region is represented by a frequency distribution with a large variation like a distribution curve $L_{100}$ as illustrated in FIG. 3 and if a standard deviation that is the determination value is large, the determination unit 35 determines that the luminance in the region is not uniform.

Figure 4:
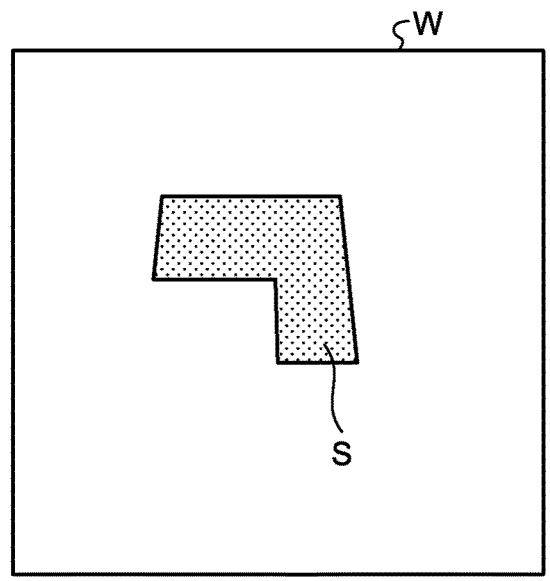
FIG. 4 is a diagram schematically illustrating an ultrasound image that is displayed by a display device of the ultrasound diagnosis system according to the first embodiment.
Figure 5:
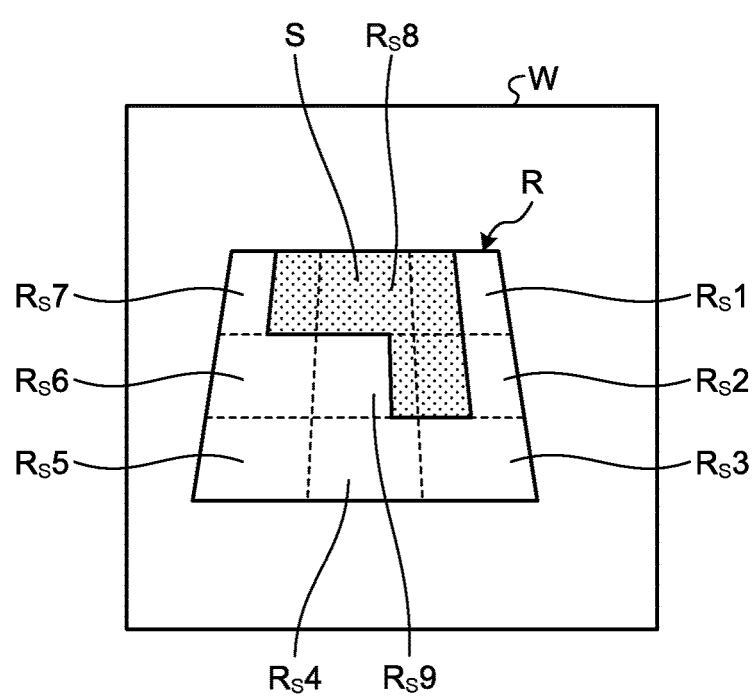
FIG. 5 is a diagram for explaining a region of interest that is set by the ultrasound observation device according to the first embodiment.

The region-of-interest setting unit 36 sets a region of interest in accordance with a preset setting condition or a region-of-interest setting instruction received by the input unit 38. FIG. 4 is a diagram schematically illustrating an ultrasound image that is displayed by the display device of the ultrasound diagnosis system according to the first embodiment. FIG. 5 is a diagram for explaining a region of interest that is set by the ultrasound observation device according to the first embodiment. The region-of-interest setting unit 36 sets, in accordance with a setting condition or input of settings, a region of interest R in a trapezoidal shape as illustrated in FIG. 5 with respect to a B-mode image W that is an ultrasound image in which an object S appears as illustrated in FIG. 4. In general, the region of interest R is set in a shape that surrounds the object S. The object S is an abnormal site, such as a tumor, when the object S is located inside a subject. The region-of-interest setting unit 36 is realized by using a general-purpose processor, such as a CPU, a dedicated integrated circuit or a custom type processor, such as an ASIC or an FPGA, which implements a specific function, or the like.

Further, the region-of-interest setting unit 36 includes a small region setting unit 361 that sets a plurality of small regions by dividing a region of interest in accordance with a preset condition, a region change unit 362 that changes a determination target region in accordance with a preset condition if the determination unit 35 determines that the region is not uniform, and a calculation region setting unit 363 that sets the determination target region as an attenuation rate calculation target region if the determination unit 35 determines that the region is uniform.

The small region setting unit 361 divides the region of interest R in accordance with a preset condition. For example, as illustrated in FIG. 5, the small region setting unit 361 divides the region of interest R by nine and sets nine small regions (small regions $R_s1$ to $R_s9$) in the region of interest R. The dividing process may be performed such that the small regions have the same area or such that the region of interest R is divided by lines along the depth direction and lines parallel to the upper base and the lower base of the region of interest R.

Figure 6:
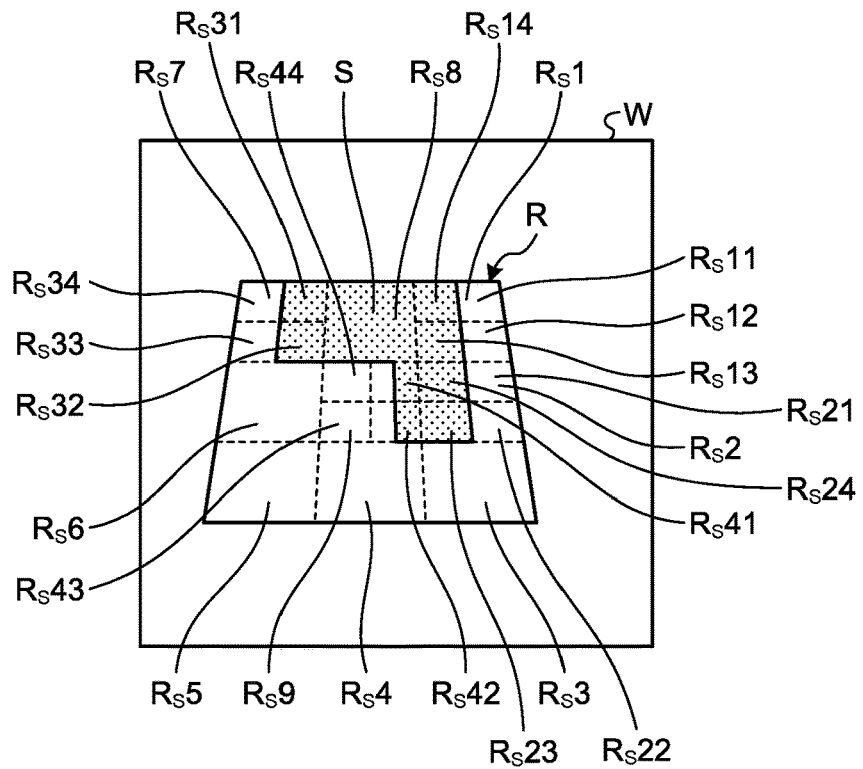
FIG. 6 is a diagram for explaining a process of setting small regions in the region of interest by the ultrasound observation device according to the first embodiment.
Figure 7:
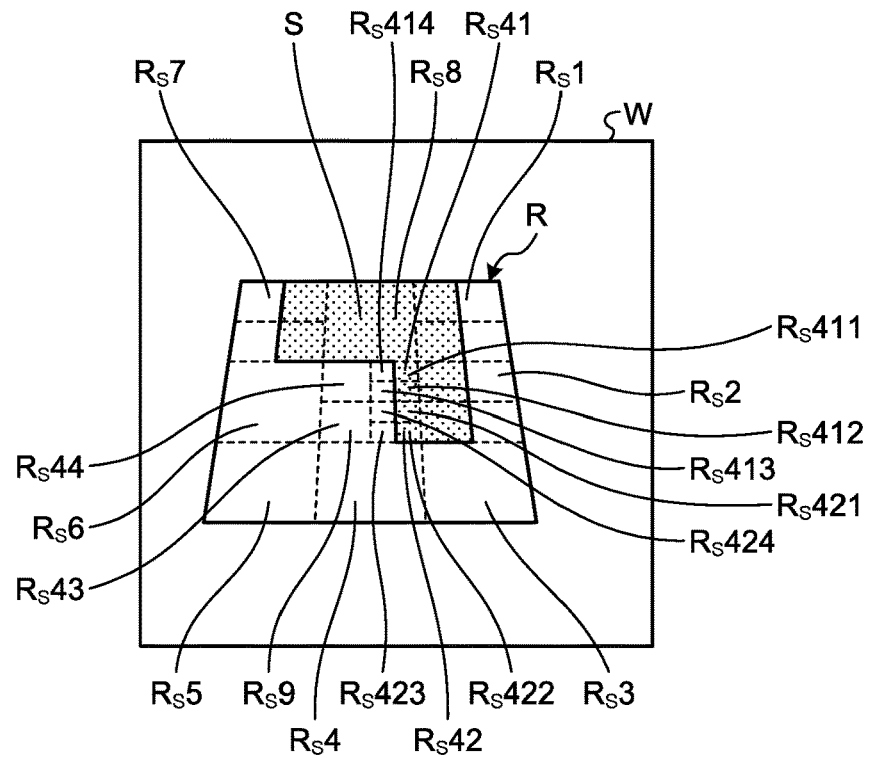
FIG. 7 is a diagram for explaining a process of setting small regions in the region of interest by the ultrasound observation device according to the first embodiment.

The region change unit 362 performs the dividing process so as to meet a division condition that is set in advance such that the determination target region is subdivided. FIG. 6 and FIG. 7 are diagrams for explaining processes of setting small regions in the region of interest by the ultrasound observation device according to the first embodiment. With respect to the small regions $R_s1$ to $R_s9$ in the region of interest R as illustrated in the FIG. 5, if the determination unit 35 determines that the small regions $R_s1$, $R_s2$, $R_s7$, and $R_s9$ are not uniform for example, the region change unit 362 divides each of the small regions $R_s1$, $R_s2$, $R_s7$, and $R_s9$. Accordingly, as illustrated in FIG. 6, divided regions $R_s11$, $R_s12$, $R_s13$, and $R_s14$ are generated in the small region $R_s1$, divided regions $R_s21$, $R_s22$, $R_s23$, and $R_s24$ are generated in the small region $R_s2$, divided regions $R_s31$, $R_s32$, $R_s33$, and $R_s34$ are generated in the small region $R_s7$, and divided regions $R_s41$, $R_s42$, $R_s43$, and $R_s44$ are generated in the small region $R_s9$.

With respect to each of the divided regions, if the determination unit 35 determines that the divided regions $R_s41$ and $R_s42$ are not uniform, the region change unit 362 further divides each of the divided regions $R_s41$ and $R_s42$. Accordingly, as illustrated in FIG. 7, divided regions $R_s411$, $R_s412$, $R_s413$, and $R_s414$ are generated in the divided region $R_s41$, and divided regions $R_s421$, $R_s422$, $R_s423$, and $R_s424$ are generated in the divided region $R_s42$. Each of the divided regions generated through the dividing process performed by the region change unit 362 corresponds to a changed small region.

In this manner, the region change unit 362 performs the dividing process on a region that is determined as not being uniform, until the size of the region reaches a minimum setting region.

The attenuation rate setting unit 37 sets an attenuation rate in each of the small regions and/or the divided regions in the region of interest set by the region-of-interest setting unit 36. The attenuation rate setting unit 37 sets the attenuation rate of each of the regions to an attenuation rate that is determined by a depth of a representative point, such as a position of the center of gravity, of each of the regions. The attenuation rate setting unit 37 is realized by using a general-purpose processor, such as a CPU, a dedicated integrated circuit or a custom type processor, such as an ASIC or an FPGA, which implements a specific function, or the like.

The input unit 38 is realized by using a user interface, such as a keyboard, a mouse, a trackball, or a touch panel, and receives input of various kinds of information. The input unit 38 outputs the received information to the control unit 40.

The storage unit 39 stores therein various programs for operating the ultrasound diagnosis system 1, data including various parameters needed for operation of the ultrasound diagnosis system 1, and the like. The storage unit 39 stores therein a threshold that is used for a determination process by the determination unit 35. Further, the storage unit 39 includes a region-of-interest setting information storage unit 391 for storing region-of-interest setting information that is information on a setting of a region of interest. The region-of-interest setting information is information for setting small regions that are obtained by dividing the region of interest, and includes information on the number of small regions to be initially set, a condition for division into the small regions, a set smallest region, and the like. The set smallest region is set to, for example, a size that is not affected by speckle having a light and dark speckled pattern.

Further, the storage unit 39 stores therein various programs including an operation program for implementing a method of operating the ultrasound diagnosis system 1. The operation program may be recorded in a computer-readable recording medium, such as a hard disk, a flash memory, a CD-ROM, a DVD-ROM, or a flexible disk, and may be widely distributed. Meanwhile, the above-described various programs may be acquired by download via a communication network. The communication network described herein is realized by, for example, a known public network, a local area network (LAN), or a wide area network (WAN), regardless of whether it is wired or wireless.

The storage unit 39 configured as described above is realized by using a read only memory (ROM) in which various programs and the like are installed in advance, a random access memory (RAM) that stores therein calculation parameters, data, and the like for each processing, and the like.

The control unit 40 controls the entire ultrasound diagnosis system 1. The control unit 40 is realized by using a CPU, various arithmetic circuits, or the like with a calculation and control function. The control unit 40 reads, from the storage unit 39, the information that is memorized and stored in the storage unit 39, and performs various kinds of arithmetic processing related to the method of operating the ultrasound observation device 3, to thereby integrate and control the ultrasound observation device 3. Meanwhile, the control unit 40 may be configured using the same CPU as the signal processing unit 32.

Figure 8:
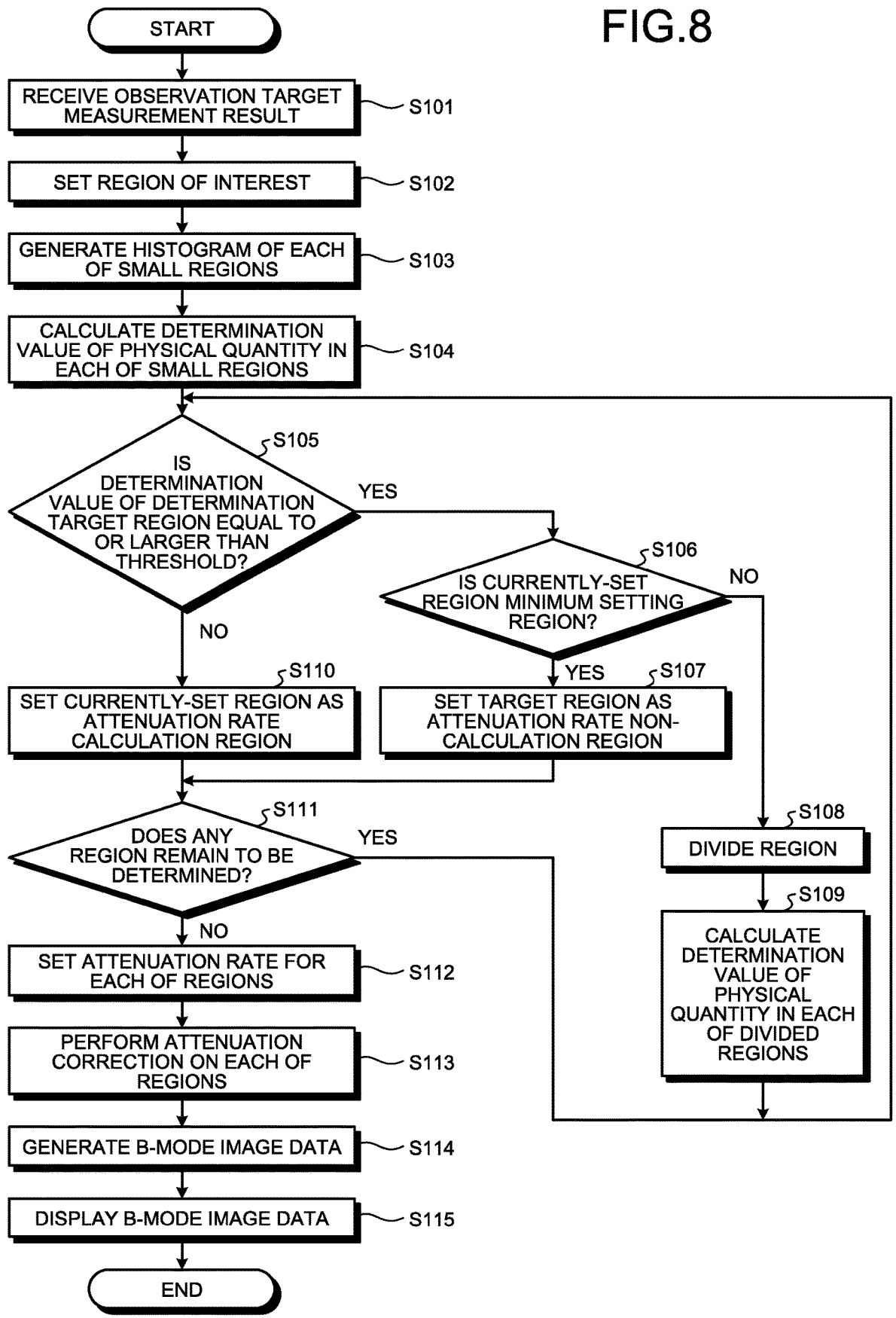
FIG. 8 is a flowchart illustrating the outline of a process performed by the ultrasound observation device according to the first embodiment.

FIG. 8 is a flowchart illustrating the outline of a process performed by the ultrasound observation device according to the first embodiment, in particular, a flowchart for explaining a process of setting an attenuation rate in a region of interest. First, the ultrasound observation device 3 receives, from the ultrasound endoscope 2, an echo signal that is an observation target measurement result obtained by the ultrasound transducer 21 (Step S101). In this case, it may be possible to display, on the display device 4, a B-mode image that is an ultrasound image based on the obtained echo signal, in preparation for a next step of setting a region of interest.

At Step S102 following Step S101, the region-of-interest setting unit 36 sets a region of interest in accordance with a preset setting condition or a region-of-interest setting instruction received by the input unit 38. In this case, the small region setting unit 361 sets small regions in the set region of interest.

At Step S103 following Step S102, the determination value calculation unit 34 generates a histogram of luminance with respect to a frequency in each of the regions set in the region of interest. Thereafter, the determination value calculation unit 34 calculates a determination value of a physical quantity (Step S104). The determination value in the first embodiment is a variation of luminance in the histogram. Hereinafter, the regions indicate the small regions or the divided regions.

Thereafter, the determination unit 35 compares the determination value of a determination target region and a threshold stored in the storage unit 39, and determines whether the determination value is equal to or larger than the threshold (Step S105). If the determination unit 35 determines that the determination value is equal to or larger than the threshold (Step S105: Yes), the determination unit 35 determines that the target small region is not uniform and proceeds to Step S106.

At Step S106, the region change unit 362 determines whether a currently-set size of the determination target region corresponds to a minimum setting region. In this case, if the region change unit 362 determines that the determination target region is the minimum setting region (Step S106: Yes), the process proceeds to Step S107.

At Step S107, the region change unit 362 sets the target region as an attenuation rate non-calculation region and proceeds to Step S111.

In contrast, if the region change unit 362 determines that the determination target region is not the minimum setting region (Step S106: No), the process proceeds to Step S108.

At Step S108, the region change unit 362 further divides the target region. For example, as illustrated in FIG. 6, the region change unit 362 generates the divided regions $R_s11$, $R_s12$, $R_s13$, and $R_s14$ by dividing the small region $R_s1$.

Thereafter, the determination value calculation unit 34 calculates a determination value in each of the divided regions (Step S109). After the determination value is calculated, the control unit 40 returns to Step S105 and performs the determination process as described above.

In contrast, at Step S105, if the determination unit 35 determines that the determination value is not equal to or larger than the threshold (Step S105: No), the determination unit 35 determines that the target small region is uniform and proceeds to Step S110.

At Step S110, the calculation region setting unit 363 sets the currently-set region as an attenuation rate calculation region. After the attenuation rate calculation region is set, the control unit 40 proceeds to Step S111.

At Step S111, the control unit 40 determines whether any region remains to be determined. Here, if the control unit 40 determines that any region remains to be determined (Step S111: Yes), the control unit 40 returns to Step S105 and performs the above-described process on the region that remains to be determined. In contrast, if the control unit 40 determines that any region does not remain to be determined (Step S111: No), the process proceeds to Step S112.

At Step S112, the attenuation rate setting unit 37 sets an attenuation rate for each of the small regions and/or the divided regions that are set as the attenuation rate calculation regions. Meanwhile, with respect to a region that is set as the attenuation rate non-calculation region, the attenuation rate setting unit 37 sets the attenuation rate of the attenuation rate non-calculation region by using attenuation rates that are set in surrounding regions. For example, the attenuation rate setting unit 37 may calculate an average of attenuation rates of adjacent regions, and adopt the average as the attenuation rate. In this case, the attenuation rates may be weighted in accordance with sizes of the regions.

Thereafter, the signal processing unit 32 performs attenuation correction on each of the regions by using the set attenuation rate (Step S113).

The image processing unit 33 acquires B-mode reception data subjected to the attenuation correction, and generates B-mode image data including a B-mode image that is an ultrasound image (Step S114).

When the B-mode image data is generated, the control unit 40 causes the display device 4 to display a B-mode image corresponding to the B-mode image data (Step S115).

In the first embodiment as described above, whether luminance is uniform is determined for each of regions that are set in a region of interest, the regions are divided in accordance with a determination result, and an attenuation rate is set for a region in which the luminance is uniform. Therefore, it is possible to maintain the size of the region of interest and appropriately set the attenuation rate in the region of interest. With use of the attenuation rate that is set as described above, it is possible to generate an ultrasound image with high accuracy.

In the first embodiment as described above, the shape of the region of interest is not limited to a trapezoid, and maybe a rectangle, a circle, an ellipse, or the like.

Second Embodiment

Figure 9:
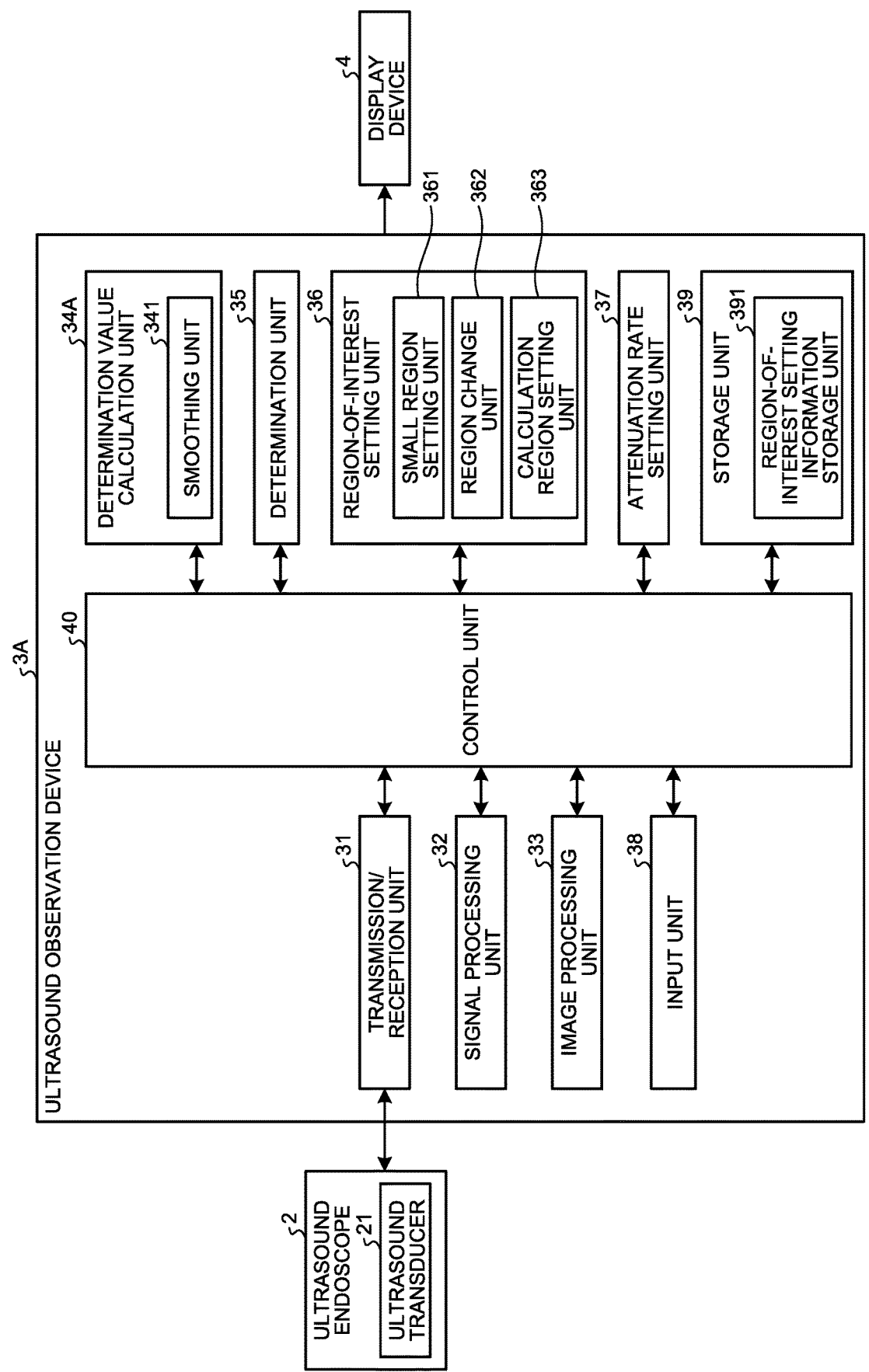
FIG. 9 is a block diagram illustrating a configuration of an ultrasound diagnosis system including an ultrasound observation device according to a second embodiment.

A second embodiment will be described below. FIG. 9 is a block diagram illustrating a configuration of an ultrasound diagnosis system including an ultrasound observation device according to the second embodiment. An ultrasound diagnosis system 1A illustrated in FIG. 9 includes an ultrasound observation device 3A instead of the ultrasound observation device 3 of the ultrasound diagnosis system 1 as described above. The ultrasound observation device 3A includes a determination value calculation unit 34A instead of the determination value calculation unit 34 as described above. Other configurations are the same as those of the ultrasound diagnosis system 1. The determination value calculation unit 34A will be described below.

The determination value calculation unit 34A calculates a determination value of a calculation region by using a preset physical quantity. In the second embodiment, luminance is used as the physical quantity and a histogram of luminance with respect to a frequency in a small region, which is set in a region of interest, or in a divided region, which is set by dividing the small region, is generated by using the luminance as the physical quantity.

Figure 10:
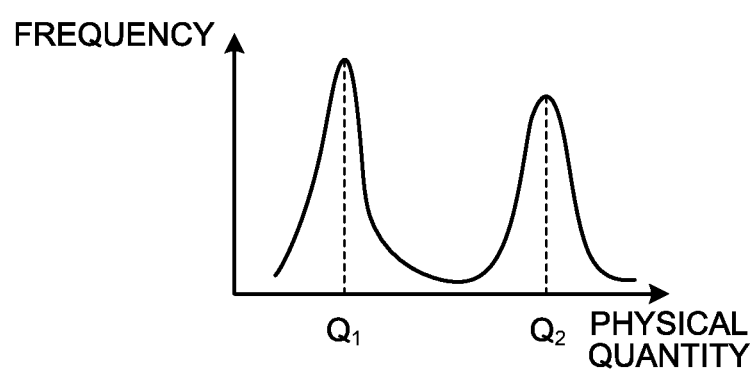
FIG. 10 is a diagram illustrating a frequency distribution with a plurality of local maximum values.

The determination value calculation unit 34A includes a smoothing unit 341. The smoothing unit 341 performs smoothing of the histogram generated by the determination value calculation unit 34A. The smoothing unit 341 is configured by using, for example, a moving average filter or the like. As the smoothed histogram, for example, a histogram with a single local maximum value (see FIG. 2) or a histogram with a plurality of local maximum values is obtained. FIG. 10 is a diagram illustrating a frequency distribution with a plurality of local maximum values. For example, as illustrated in FIG. 10, a histogram with local maximum values with respect to physical quantities $Q_1$ and $Q_2$ ($Q_1 < Q_2$) is obtained.

The determination value calculation unit 34A calculates, as a determination value, the number of local maximum values in the histogram that is smoothed by the smoothing unit 341. In this case, the determination value calculation unit 34A counts the number of local maximum values that are equal to or larger than a preset frequency.

The determination unit 35 determines whether luminance in a determination target small region or a determination target divided region is uniform based on the number of local maximum values that is the determination value calculated by the determination value calculation unit 34A and a preset threshold. The threshold is the number of local maximum values and is set to one in the second embodiment. Specifically, the determination unit 35 determines whether the determination value is larger than the preset threshold, and determines that the luminance is uniform if the number of local maximum values is zero or one, for example. In contrast, if the number of local maximum values exceeds one, the determination unit 35 determines that the luminance is not uniform. For example, the determination unit 35 determines that the luminance is uniform if a histogram with the distribution curve $L_1$ as illustrated in FIG. 2 is obtained and the frequency of the local maximum value is equal to or larger than a set frequency, and determines that the luminance is not uniform if a histogram with the distribution curve $L_{100}$ as illustrated in FIG. 3 is obtained.

Figure 11:
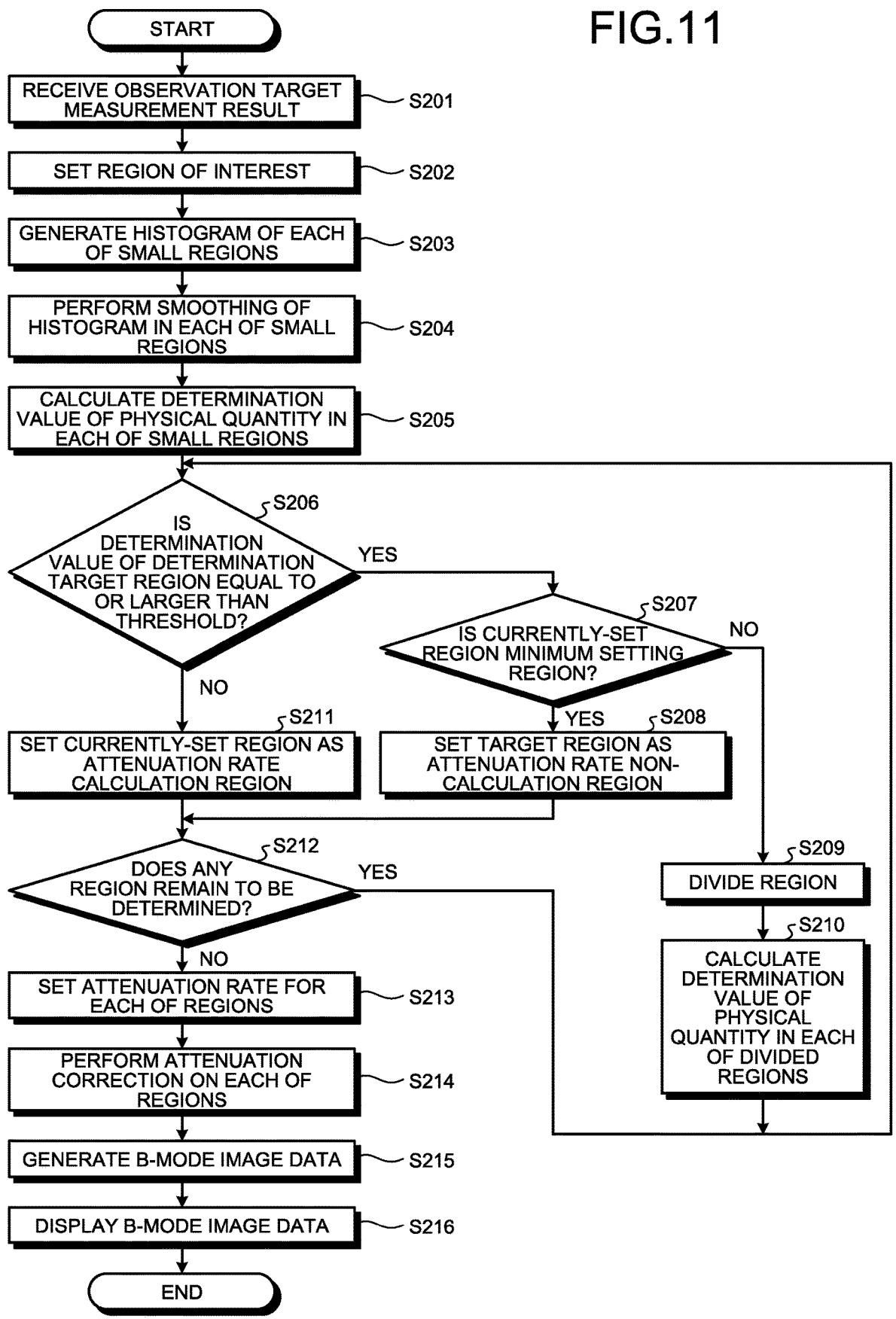
FIG. 11 is a flowchart illustrating the outline of a process performed by the ultrasound observation device according to the second embodiment.

FIG. 11 is a flowchart illustrating the outline of a process performed by the ultrasound observation device according to the second embodiment, in particular, a flowchart for explaining a process of setting an attenuation rate in a region of interest. First, similarly to the flowchart illustrated in FIG. 8 as described above, the ultrasound observation device 3 receives, from the ultrasound endoscope 2, an echo signal that is an observation target measurement result obtained by the ultrasound transducer 21 (Step S201), and the region-of-interest setting unit 36 sets a region of interest in accordance with a preset setting condition or a region-of-interest setting instruction received by the input unit 38 (Step S202).

At Step S202, the small region setting unit 361 sets a plurality of small regions by dividing the set region of interest.

At Step S203 following Step S202, the determination value calculation unit 34A generates a histogram of luminance with respect to a frequency in each of the regions set in the region of interest (Step S203).

When the histogram is generated, the smoothing unit 341 performs smoothing of the histogram (Step S204).

Thereafter, the determination value calculation unit 34A calculates a determination value of a physical quantity (Step S205). The determination value in the second embodiment is the number of local maximum values in the smoothed histogram.

The determination unit 35 compares the determination value of a determination target region and a threshold stored in the storage unit 39, and determines whether the determination value is equal to or larger than the threshold (Step S206). If the determination unit 35 determines that the determination value is equal to or larger than the threshold (Step S206: Yes), the determination unit 35 determines that the target small region is not uniform and proceeds to Step S207.

At Step S207, the region change unit 362 determines whether a currently-set size of the determination target region corresponds to a minimum setting region. In this case, if the region change unit 362 determines that the determination target region is the minimum setting region (Step S207: Yes), the process proceeds to Step S208.

At Step S208, the region change unit 362 sets the target region as an attenuation rate non-calculation region and proceeds to Step S212.

In contrast, if the region change unit 362 determines that the determination target region is not the minimum setting region (Step S207: No), the region change unit 362 further divides the target region (Step S209).

Thereafter, the determination value calculation unit 34A calculates a determination value in each of the divided regions (Step S210). After the determination value is calculated, the control unit 40 returns to Step S206 and performs the determination process as described above.

In contrast, at Step S206, if the determination unit 35 determines that the determination value is not equal to or larger than the threshold (Step S206: No), the determination unit 35 determines that the target small region is uniform and proceeds to Step S211.

At Step S211, the calculation region setting unit 363 sets the currently-set region as an attenuation rate calculation region. After the attenuation rate calculation region is set, the control unit 40 proceeds to Step S212.

At Step S212, the control unit 40 determines whether any region remains to be determined. Here, if the control unit 40 determines that any region remains to be determined (Step S212: Yes), the control unit 40 returns to Step S206 and performs the above-described process on the region that remains to be determined. In contrast, if the control unit 40 determines that any region does not remain to be determined (Step S212: No), the process proceeds to Step S213.

At Step S213, the attenuation rate setting unit 37 sets an attenuation rate for each of the small regions and/or the divided regions that are set as the attenuation rate calculation regions. Thereafter, the signal processing unit 32 performs attenuation correction on each of the regions by using the set attenuation rate (Step S214).

The image processing unit 33 acquires B-mode reception data subjected to the attenuation correction, and generates B-mode image data indicating a B-mode image that is an ultrasound image (Step S215). When the B-mode image data is generated, the control unit 40 causes the display device 4 to display the B-mode image data (Step S216).

In the second embodiment as described above, whether luminance is uniform is determined for each of regions that are set in a region of interest, the regions are divided in accordance with a determination result, and an attenuation rate is set for a region in which the luminance is uniform. Therefore, it is possible to maintain the size of the region of interest and appropriately set the attenuation rate in the region of interest. With use of the attenuation rate that is set as described above, it is possible to generate an ultrasound image with high accuracy.

Third Embodiment

Figure 12:
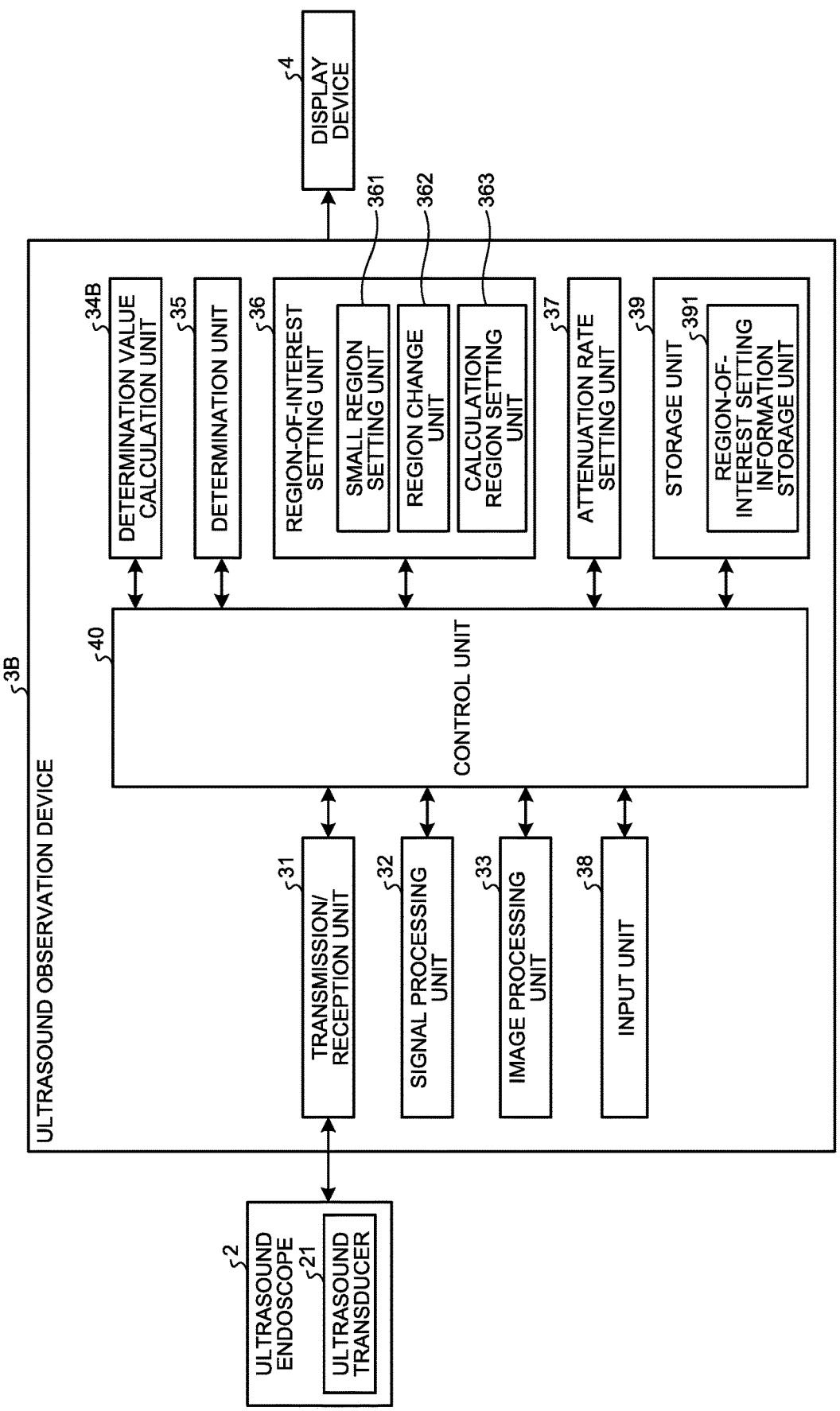
FIG. 12 is a block diagram illustrating a configuration of an ultrasound diagnosis system including an ultrasound observation device according to a third embodiment.

A third embodiment will be described below. FIG. 12 is a block diagram illustrating a configuration of an ultrasound diagnosis system including an ultrasound observation device according to the third embodiment. An ultrasound diagnosis system 1B illustrated in FIG. 12 includes an ultrasound observation device 3B instead of the ultrasound observation device 3 of the ultrasound diagnosis system 1 as described above. The ultrasound observation device 3B includes a determination value calculation unit 34B instead of the determination value calculation unit 34 as described above. Other configurations are the same as those of the ultrasound diagnosis system 1. The determination value calculation unit 34B will be described below.

The determination value calculation unit 34B calculates a determination value of a calculation region by using a preset physical quantity. In the third embodiment, luminance is used as the physical quantity and a histogram of luminance with respect to a frequency in a small region, which is set in a region of interest, or in a divided region, which is set by dividing the small region, is generated by using the luminance as the physical quantity. If the generated histogram includes a plurality of local maximum values that are equal to or larger than a preset frequency, the determination value calculation unit 34B calculates a difference between the physical quantities indicating the local maximum values, and adopts the difference as the determination value. For example, if the histogram as illustrated in FIG. 10 is obtained, the determination value calculation unit 34B calculates a difference between the physical quantity $Q_1$ and the physical quantity $Q_2$ ($Q_2-Q_1$). Meanwhile, if the number of local maximum values is zero or one, the determination value calculation unit 34B sets the above-described difference to zero. If the histogram includes three or more local maximum values, the determination value calculation unit 34B calculates differences between physical quantities corresponding to adjacent local maximum values, and calculates the determination value based on the differences.

The determination unit 35 determines whether luminance in a determination target small region or a determination target divided region is uniform based on the physical quantity difference that is the determination value calculated by the determination value calculation unit 34B and a preset threshold. The threshold is a physical quantity difference that can be regarded as uniform. Specifically, the determination unit 35 determines whether the determination value is larger than the preset threshold, and determines that the luminance is uniform if the difference is equal to or smaller than the threshold. In contrast, the determination unit 35 determines that the luminance is not uniform if the difference is larger than the threshold.

The process of setting the attenuation rate in the region of interest is performed in accordance with Steps S201, S202, and S204 to S216 in FIG. 11 as described above. In this case, the determination value is replaced with the physical quantity difference and the threshold is replaced with the above-described threshold. Meanwhile, it may be possible to perform smoothing of the histogram by combining the technique of the second embodiment as described above. In this case, the process of setting the attenuation rate in the region of interest is performed in accordance with Step S201 to S216 in FIG. 11.

In the third embodiment as described above, whether luminance is uniform is determined based on the physical quantity difference in the histogram for each of regions that are set in the region of interest, the regions are divided in accordance with a determination result, and an attenuation rate is set for a region in which the luminance is uniform. Therefore, it is possible to maintain the size of the region of interest and appropriately set the attenuation rate in the region of interest. With use of the attenuation rate that is set as described above, it is possible to generate an ultrasound image with high accuracy.

Fourth Embodiment

Figure 13:
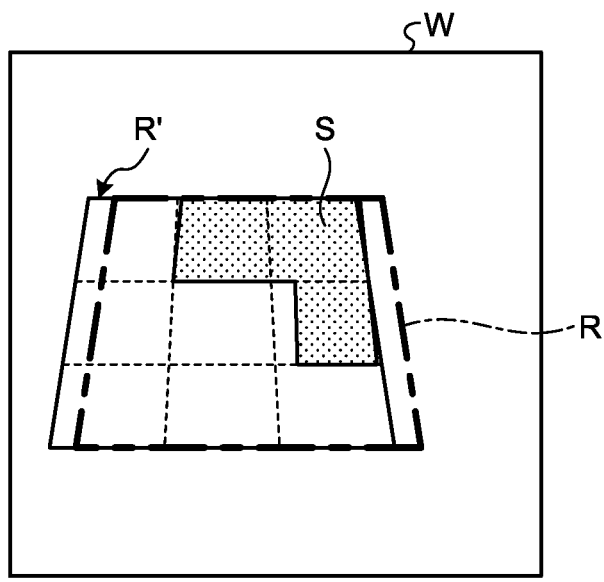
FIG. 13 is a diagram for explaining a process of setting small regions in a region of interest by an ultrasound observation device according to a fourth embodiment.

A fourth embodiment will be described below. FIG. 13 is a diagram for explaining a process of setting small regions in a region of interest by an ultrasound observation device according to the fourth embodiment. In the first to the third embodiments as described above, if it is determined that luminance of the determination target region is not uniform, the region is divided; however, in the fourth embodiment, the size of the region of interest is maintained and the region is moved. In the fourth embodiment, it is assumed that an ultrasound diagnosis system has the same configuration as the ultrasound diagnosis system 1.

For example, as illustrated in FIG. 13, if the determination unit 35 determines that any of small regions divided by dashed lines in a region of interest R is not uniform, the region change unit 362 moves the region of interest R. In this case, the region change unit 362 moves the region of interest R in a preset direction by a preset number of pixels. For example, in FIG. 13, the region is moved leftward by a few pixels in the figure. Accordingly, arrangement of the small regions in the B-mode image is set again. In this manner, the region change unit 362 performs a change process so as to meet a condition that is set for moving a determination region.

The determination value calculation unit 34 calculates a determination value of each of small regions in a moved region of interest R' indicated by a chain line. The determination unit 35 determines whether each of the small regions in the region of interest R' is uniform based on the calculated determination value.

In the fourth embodiment, as described above, calculation of the determination value in the region of interest, determination on whether the region is uniform, and movement of the region of interest are repeated. Meanwhile, if the region of interest does not become uniform after being moved more than a preset number of times of movement, the region change unit 362 may adopt a region of interest including the largest number of small regions that are determined as being uniform among the regions of interest that are obtained by moving the set region of interest, or may output warning information for requesting an operator to set the region of interest again.

If the region of interest is confirmed, the ultrasound observation device 3 sets the attenuation rate and generates the B-mode image as described above.

In the fourth embodiment as described above, whether luminance is uniform is determined for each of regions that are set in the region of interest, the region is moved in accordance with a determination result, and an attenuation rate is set for each of small regions of the confirmed region of interest. Therefore, it is possible to maintain the size of the region of interest and appropriately set the attenuation rate in the region of interest. With use of the attenuation rate that is set as described above, it is possible to generate an ultrasound image with high accuracy.

Meanwhile, the first to the fourth embodiments as described above may be combined appropriately. For example, it may be possible to perform smoothing of a histogram, calculate a local maximum value difference of the histogram, divides a region into small regions, and move the small regions by combining the technique of the fourth embodiment.

Fifth Embodiment

Figure 14:
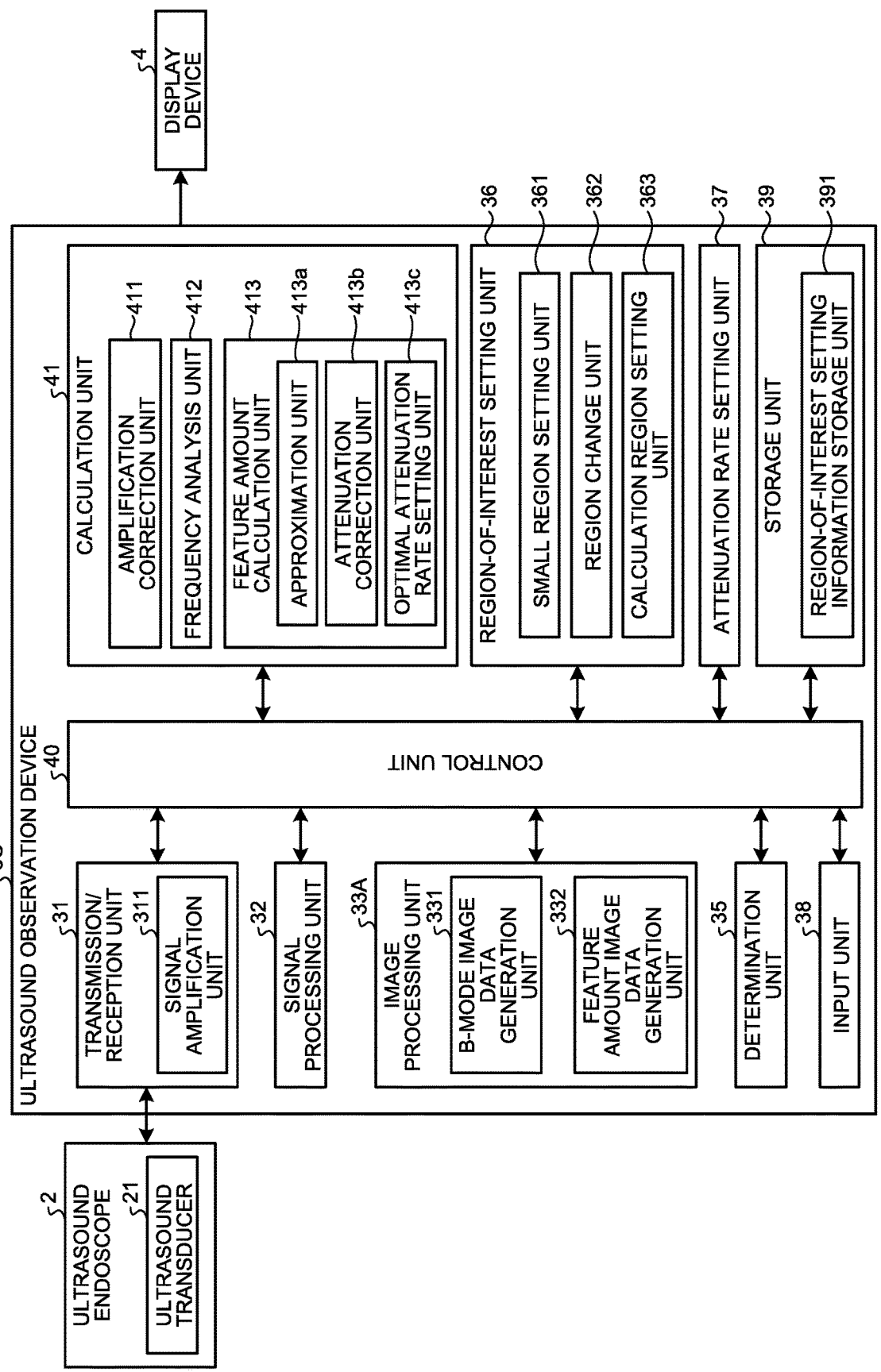
FIG. 14 is a block diagram illustrating a configuration of an ultrasound diagnosis system including an ultrasound observation device according to a fifth embodiment.

A fifth embodiment will be descried below. FIG. 14 is a block diagram illustrating a configuration of an ultrasound diagnosis system including an ultrasound observation device according to the fifth embodiment. An ultrasound diagnosis system 1C illustrated in FIG. 14 includes an ultrasound observation device 3C instead of the ultrasound observation device 3 of the ultrasound diagnosis system 1 as described above. The ultrasound observation device 3C includes an image processing unit 33A instead of the image processing unit 33 and includes a calculation unit 41 instead of the determination value calculation unit 34, as compared to the configuration of the ultrasound observation device 3 as described above. The calculation unit 41 functions as the determination value calculation unit. Further, it is assumed that the transmission/reception unit 31 includes a signal amplification unit 311. Other configurations are the same as those of the ultrasound diagnosis system 1. The transmission/reception unit 31, the image processing unit 33A, and the calculation unit 41 will be described below.

Figure 15:
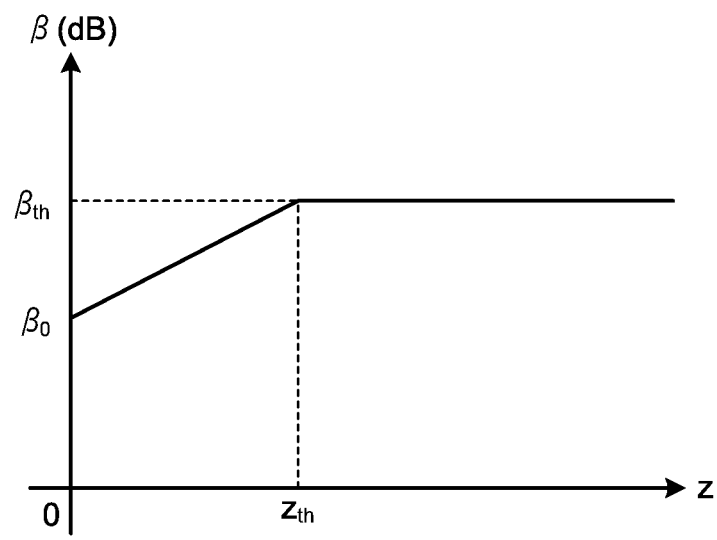
FIG. 15 is a diagram illustrating a relationship between a reception depth and an amplification factor in an amplification process performed by a signal amplification unit of the ultrasound observation device according to the fifth embodiment.

The transmission/reception unit 31 includes the signal amplification unit 311 that amplifies an echo signal. The signal amplification unit 311 performs sensitivity time control (STC) correction for performing amplification at a higher amplification factor on an echo signal with a larger reception depth. FIG. 15 is a diagram illustrating a relationship between the reception depth and the amplification factor in an amplification process performed by the signal amplification unit 311. A reception depth z illustrated in FIG. 15 is a quantity that is calculated based on an elapsed time since start of reception of ultrasound waves. As illustrated in FIG. 15, an amplification factor $\beta$ (dB) linearly increases from $\beta_0$ to $\beta_{th}$ ($>\beta_0$) with an increase of the reception depth z when the reception depth z is smaller than a threshold $z_{th}$. Further, the amplification factor $\beta$ (dB) has a constant value $\beta_{th}$ when the reception depth z is equal to or larger than the threshold $z_{th}$. A value of the threshold $z_{th}$ is set such that an almost whole ultrasound signal received from an observation target is attenuated and noise becomes dominant. More generally, it is sufficient that the amplification factor $\beta$ monotonically increases with an increase of the reception depth z if the reception depth z is smaller than the threshold $z_{th}$. Meanwhile, the relationship illustrated in FIG. 15 is stored in advance in the storage unit 39.

The transmission/reception unit 31 performs processing, such as filtering, on the echo signal amplified by the signal amplification unit 311, subsequently performs A/D conversion to generate RF data in the time domain, and outputs the RF data to the signal processing unit 32, the calculation unit 41, and the storage unit 39. Meanwhile, if the ultrasound endoscope 2 is configured to cause the ultrasound transducer 21, in which a plurality of elements are arranged in an array manner, to electronically perform scanning, the transmission/reception unit 31 includes a multi-channel circuit for beam synthesis corresponding to a plurality of elements.

It is preferable to set various processing frequency bands of the echo signal in the signal amplification unit 311 to a wide band that covers almost the whole linear response frequency band that is used for acoustoelectric conversion from an ultrasound echo to an echo signal in the ultrasound transducer 21. With this configuration, when a frequency spectrum approximation process (to be described later) is performed, it is possible to perform approximation with accuracy.

The calculation unit 41 includes an amplification correction unit 411 that performs amplification correction on the RF data generated by the transmission/reception unit 31 such that the amplification factor $\beta$ becomes uniform regardless of the reception depth, a frequency analysis unit 412 that analyzes a frequency by performing fast Fourier transform (FFT) on the RF data subjected to the amplification correction and calculates a frequency spectrum, and a feature amount calculation unit 413 that calculates a feature amount of the frequency spectrum. The calculation unit 41 is realized by using a general-purpose processor, such as a CPU, a dedicated integrated circuit or a custom type processor, such as an ASIC or an FPGA, which implements a specific function, or the like.

Figure 16:
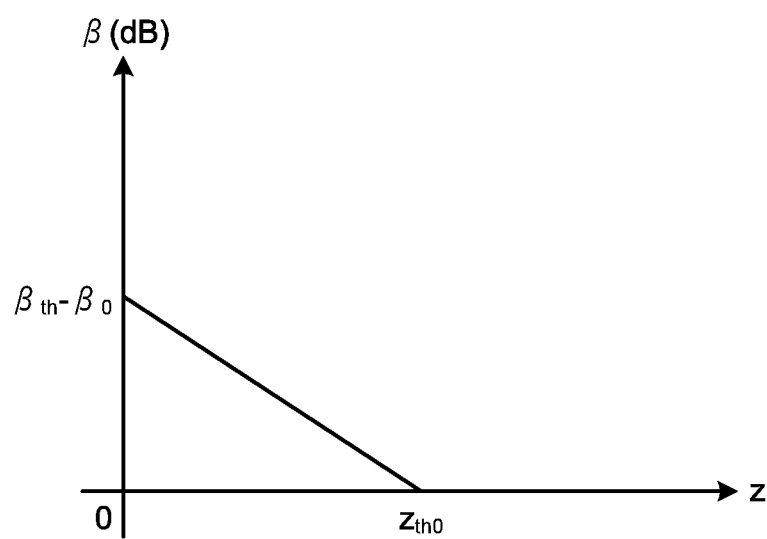
FIG. 16 is a diagram illustrating a relationship between a reception depth and an amplification factor in an amplification correction process performed by an amplification correction unit of the ultrasound observation device according to the fifth embodiment.

FIG. 16 is a diagram illustrating a relationship between the reception depth and the amplification factor in an amplification correction process performed by the amplification correction unit 411. As illustrated in FIG. 16, the amplification factor $\beta$ (dB) in the amplification correction process performed by the amplification correction unit 411 has a maximum value $\beta_{th}-\beta_0$ when the reception depth z is zero, linearly decreases until the reception depth z reaches a threshold $z_{th0}$ from zero, and has a value of zero when the reception depth z is equal to or larger than the threshold $z_{th0}$. By causing the amplification correction unit 411 to perform amplification correction on a digital RF signal using the amplification factor that is determined as described above, it is possible to compensate for the influence of the STC correction performed by the signal processing unit 32 and output a signal with the uniform amplification factor $\beta_{th}$. Meanwhile, a relationship between the reception depth z and the amplification factor $\beta$ used by the amplification correction unit 411 varies, of course, depending on the relationship between the reception depth and the amplification factor used by the signal processing unit 32.

The reason why the amplification correction as described above is performed will be described. The STC correction is a correction process of eliminating the influence of attenuation from the amplitude of an analog signal waveform by uniformly amplifying the amplitude of the analog signal waveform over the whole frequency band and amplifying the depth using an amplification factor that monotonically increases. Therefore, when the B-mode image, in which the amplitude of the echo signal is converted to and displayed as luminance, is generated and if uniform tissue is scanned, the luminance becomes uniform regardless of the depth due to execution of the STC correction. In other words, it is possible to achieve an effect to eliminate the influence of attenuation from a luminance value of the B-mode image.

In contrast, when a result of calculation and analysis of an ultrasound frequency spectrum is used as in the fifth embodiment, even if the STC correction is performed, it is not always possible to correctly eliminate the influence of attenuation due to propagation of ultrasound waves. This is because an attenuation amount generally varies depending on a frequency (see Equation (1) to be described later), but the amplification factor in the STC correction varies depending on only a distance and is independent of a frequency.

To solve the problem as described above, that is, the problem that when the result of calculation and analysis of the ultrasound frequency spectrum is used, it is not always possible to correctly eliminate the influence due to propagation of the ultrasound waves even if the STC correction is performed, it may be possible to output a reception signal that is subjected to the STC correction when generating the B-mode image and it may be possible to perform new transmission different from transmission for generation of the B-mode image and output a reception signal that is not subjected to the STC correction when generating an image based on the frequency spectrum. However, in this case, there is a problem that a frame rate of image data that is generated based on the reception signal is reduced.

Therefore, in the fifth embodiment, to maintain the frame rate of image data to be generated and eliminate the influence of the STC correction on a signal that is subjected to the STC correction for the B-mode image, the amplification correction unit 411 corrects the amplification factor.

The frequency analysis unit 412 performs, at predetermined time intervals, sampling of RF data of each of sound rays that are subjected to amplification correction by the amplification correction unit 411, and generates sample data. The frequency analysis unit 412 calculates frequency spectrums at a plurality of portions on the RF data (data positions) by performing an FFT process on a sample data group. The "frequency spectrum" described herein means a "frequency distribution with respect to an intensity at a certain reception depth z" and is obtained by performing the FFT process on the sample data group. Further, the "intensity" described herein indicate any of a parameter, such as a voltage of an echo signal, electric power of the echo signal, sound pressure of an ultrasound echo, or acoustic energy of the ultrasound echo, an amplitude or a time-integral value of the parameter, and any combination of the above-described values.

In general, when an observation target is living tissue, the frequency spectrum indicates a different tendency depending on the property of the living tissue scanned by ultrasound waves. This is because the frequency spectrum is correlated with a size, a number density, acoustic impedance, or the like of a scatterer that causes ultrasound waves to scatter. The "property of the living tissue" described herein is, for example, a malignant tumor (cancer), a benign tumor, an endocrine tumor, a mucinous tumor, normal tissue, a cyst, a vascular channel, or the like.

Figure 17:
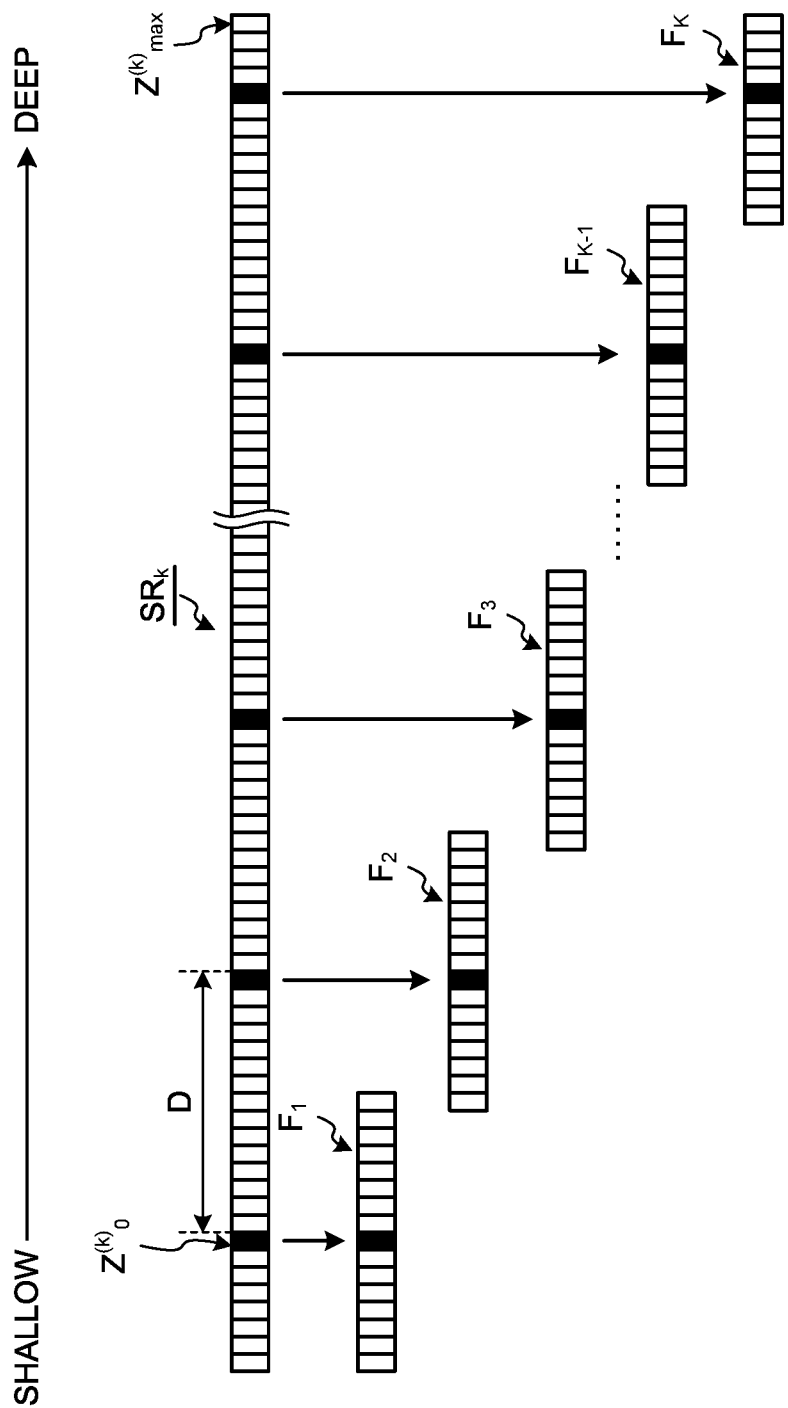
FIG. 17 is a diagram schematically illustrating a data array in a single sound ray of an ultrasound signal.

FIG. 17 is a diagram schematically illustrating a data array in a single sound ray of an ultrasound signal. In a sound ray $SR_k$ illustrated in FIG. 17, each of white and black rectangles indicates data at a single sample point. Further, in the sound ray $SR_k$, data located at a more rightward position indicates sample data in a deeper portion measured from the ultrasound transducer 21 along the sound ray $SR_k$ (see arrows in FIG. 17). The sound ray $SR_k$ is discretized at time intervals corresponding to a sampling frequency (for example, 50 MHz) that is adopted in A/D conversion performed by the transmission/reception unit 31. In FIG. 17, a case is illustrated in which an eighth data position in the sound ray $SR_k$ numbered k is set as an initial value $Z^{(k)}_0$ in a direction of the reception depth z, but it is possible to arbitrarily set the position of the initial value. A result of calculation performed by the frequency analysis unit 412 is obtained as a complex number, and stored in the storage unit 39.

A data group $F_j$ (j=1, 2, ..., K) illustrated in FIG. 17 is a sample data group to be subjected to the FFT process. In general, to perform the FFT process, the sample data group needs to have the same number of pieces of data as a power of two. In this regard, the sample data group $F_j$ (j=1, 2, ..., K−1) has 16 (=$2^4$) pieces of data and therefore is a normal data group, whereas a sample data group $F_K$ has 12 pieces of data and therefore is an abnormal data group. When the FFT process is to be performed on the abnormal data group, a process of generating a normal sample data group by inserting the same number of pieces of zero data as pieces of deficient data is performed. This will be described in detail later together with describing the process performed by the frequency analysis unit 412 (see FIG. 21).

Figure 18:
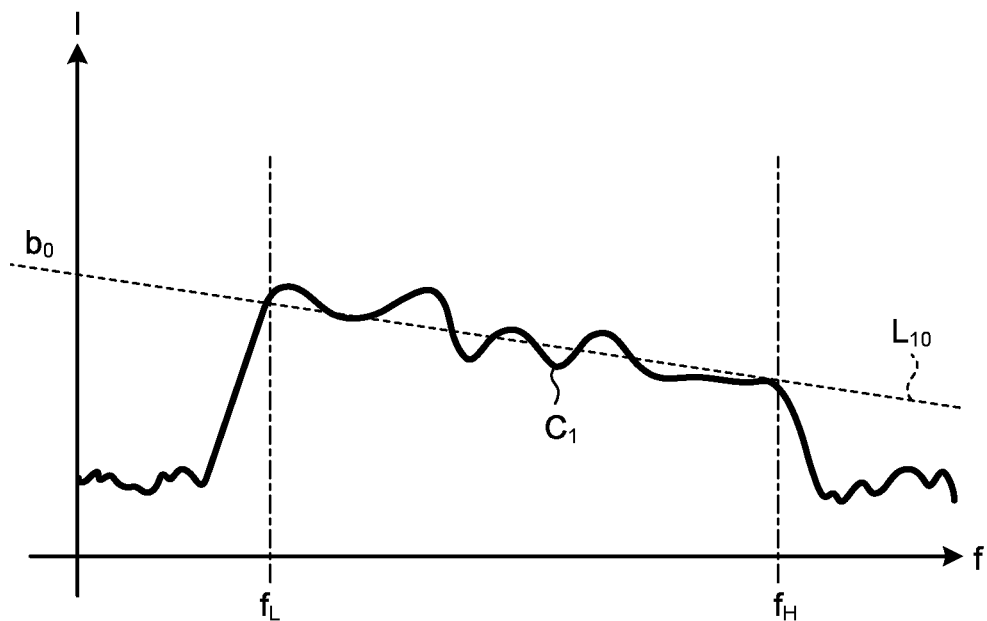
FIG. 18 is a diagram illustrating an example of a frequency spectrum calculated by a frequency analysis unit of the ultrasound observation device according to the fifth embodiment.

FIG. 18 is a diagram illustrating an example of the frequency spectrum calculated by the frequency analysis unit 412. In FIG. 18, the horizontal axis represents a frequency f. Further, in FIG. 18, the vertical axis represents a common logarithm (decibel representation) I=10 $\log_{10}$ ($I_0/I_c$) of an amount that is obtained by dividing an intensity $I_0$ by a reference intensity $I_c$ (constant). A regression line $L_{10}$ (hereinafter, also simply referred to as the line $L_{10}$) illustrated in FIG. 18 will be described later. In the fifth embodiment, a curve and a line are formed of a set of discrete points.

In a frequency spectrum $C_1$ illustrated in FIG. 18, a lower limit frequency $f_L$ and an upper limit frequency $f_H$ of a frequency band to be used in calculations described below are parameters that are determined based on a frequency band of the ultrasound transducer 21, a frequency band of a pulse signal transmitted by the transmission/reception unit 31, or the like. Hereinafter, a frequency band determined by the lower limit frequency $f_L$ and the upper limit frequency $f_H$ in FIG. 18 will be referred to as a "frequency band F".

The feature amount calculation unit 413 calculates a feature amount of each of frequency spectrums, calculates a corrected feature amount of each of the frequency spectrums by performing attenuation correction of eliminating the influence of attenuation of ultrasound waves from the feature amount of each of the frequency spectrums (hereinafter, referred to as a pre-corrected feature amount) with respect to each of attenuation rate candidate values that give different attenuation properties when the ultrasound waves propagate through an observation target, and sets an optimal attenuation rate for the observation target from among the attenuation rate candidate values by using the corrected feature amount.

The feature amount calculation unit 413 includes an approximation unit 413a that approximates a frequency spectrum by a line and calculates a feature amount of the frequency spectrum in a case before the attenuation correction process is performed, an attenuation correction unit 413b that calculates a feature amount by performing attenuation correction on the pre-corrected feature amount calculated by the approximation unit 413a, and an optimal attenuation rate setting unit 413c that sets an optimal attenuation rate from among a plurality of attenuation rate candidate values based on a statistical variation of the corrected feature amounts that are calculated for all of the frequency spectrums by the attenuation correction unit 413b.

The approximation unit 413a approximates a frequency spectrum by a linear expression (regression line) by performing regression analysis on the frequency spectrum in a predetermined frequency band, and calculates a pre-corrected feature amount that characterizes the approximated linear expression. For example, in the case of the frequency spectrum $C_1$ illustrated in FIG. 18, the approximation unit 413a obtains a regression line $L_{10}$ by performing regression analysis in the frequency band F and approximating the frequency spectrum $C_1$ by a linear expression. In other words, the approximation unit 413a calculates, as a pre-corrected feature amount, a slope $a_0$ of the regression line $L_{10}$, an intercept $b_0$ of the regression line $L_{10}$, and a mid-band fit $c_0=a_0 f_M+b_0$ that is a value of a center frequency $f_M=(f_L+f_H)/2$ of the frequency band F on the regression line.

Of the three pre-corrected feature amounts, the slope $a_0$ is correlated with a size of an ultrasound scatterer and generally has a smaller value with an increase in the size of the scatterer. Further, the intercept $b_0$ is correlated with the size of the scatterer, an acoustic impedance difference, a number density (density) of the scatterer, or the like. Specifically, the intercept $b_0$ has a larger value with an increase in the size of the scatterer, with an increase in the acoustic impedance difference, and with an increase in the number density of the scatterer. The mid-band fit $c_0$ is an indirect parameter that is derived from the slope $a_0$ and the intercept $b_0$ and gives a spectrum intensity at the center of an effective frequency band. Therefore, the mid-band fit $c_0$ is regarded as being correlated with luminance of the B-mode image to some extent, in addition to the size of the scatterer, the acoustic impedance difference, and the number density of the scatterer. Meanwhile, the feature amount calculation unit 413 may approximate the frequency spectrum by a quadratic expression or a more complicated polynomial through the regression analysis.

Correction performed by the attenuation correction unit 413b will be described. In general, an attenuation amount A(f, z) of an ultrasound wave is defined as attenuation that occurs while the ultrasound wave moves back and forth between the reception depth 0 and the reception depth z and is defined as an intensity change (difference using decibel representation) before and after the movement. It is empirically known that the attenuation amount A(f, z) is proportional to the frequency in uniform tissue, and represented by Equation (1) below.

$$A(f,z)=2\alpha z f \quad (1)$$

Here, a proportional constant $\alpha$ is an amount called an attenuation rate. Further, z is a reception depth of the ultrasound wave, and f is a frequency. When the observation target is a biological body, a specific value of the attenuation rate $\alpha$ is determined depending on a region of the biological body. A unit of the attenuation rate $\alpha$ is, for example, dB/cm/MHz. Meanwhile, in the fifth embodiment, it may be possible to change the value of the attenuation rate $\alpha$ by input via the input unit 38.

The attenuation correction unit 413b performs attenuation correction according to Equations (2) to (4) below on the pre-corrected feature amounts (the slope $a_0$, the intercept $b_0$, and the mid-band fit $c_0$) extracted by the approximation unit 413a, and calculates corrected feature amounts a, b, and c.

$$a=a_0+2\alpha z \quad (2)$$

$$b=b_0 \quad (3)$$

$$c=c_0+A(f_M,z)=c_0+2\alpha z f_M(=af_M+b) \quad (4)$$

As can be seen from Equations (2) and (4), the attenuation correction unit 413b performs correction with a larger correction amount with an increase in the reception depth z of the ultrasound wave. Further, according to Equation (3), correction related to the intercept is identical transformation. This is because the intercept is a frequency component corresponding to a frequency of 0 (Hz) and is not affected by attenuation.

Figure 19:
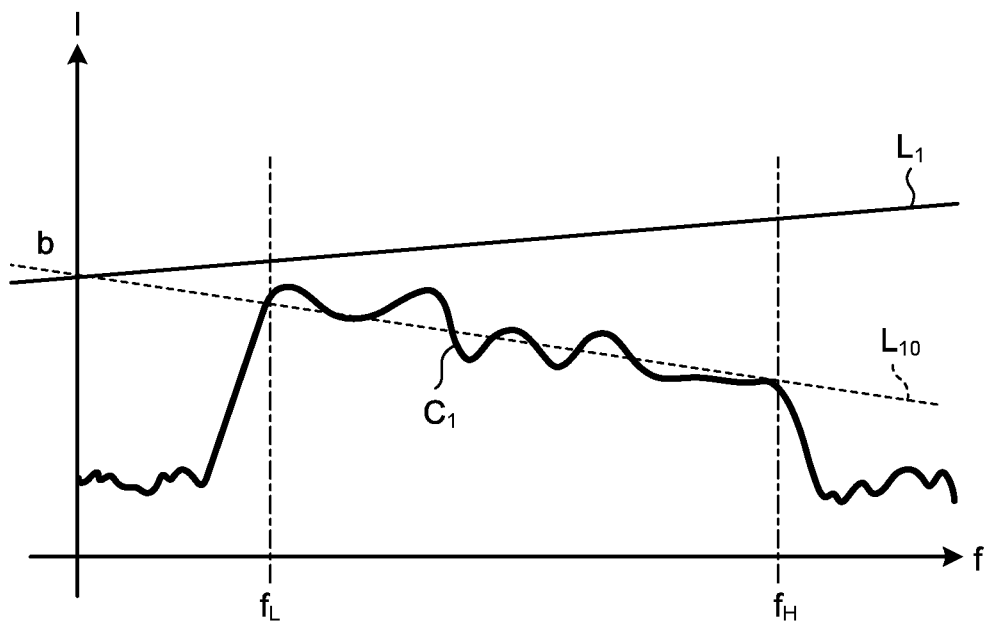
FIG. 19 is a diagram illustrating a line including, as parameters, corrected feature amounts calculated by an attenuation correction unit of the ultrasound observation device according to the fifth embodiment.

FIG. 19 is a diagram illustrating, as parameters, the corrected feature amounts a, b, and c calculated by the attenuation correction unit 413b. A line $L_1$ is represented by Equation below.

$$I=af+b=(a_0+2\alpha z)f+b_0 \quad (5)$$

As can be seen from Equation (5), the line $L_1$ has a larger slope ($a>a_0$) and the same intercept ($b=b_0$) as compared to the line $L_{10}$ that has not been subjected to the attenuation correction.

The optimal attenuation rate setting unit 413c sets, as an optimal attenuation rate, an attenuation rate candidate value for which a statistical variation of the corrected feature amount that is calculated for each of the attenuation rate candidate values with respect to all of the frequency spectrums by the attenuation correction unit 413b is minimum. In the fifth embodiment, dispersion is adopted as an amount indicating the statistical variation. In this case, the optimal attenuation rate setting unit 413c sets an attenuation rate candidate value with the smallest dispersion as an optimal attenuation rate. Of the three corrected feature amounts a, b, and c as described above, two are independent. In addition, the corrected feature amount b is independent of the attenuation rate. Therefore, when an optimal attenuation rate is to be set for the corrected feature amounts a and c, it is sufficient for the optimal attenuation rate setting unit 413c to calculate dispersion of one of the corrected feature amounts a and c.

However, it is preferable that the corrected feature amount used by the optimal attenuation rate setting unit 413c for setting the optimal attenuation rate is of the same type as the corrected feature amount that is used for generating feature amount image data by the image processing unit 33A. In other words, it is more preferable to adopt dispersion of the corrected feature amount a when the image processing unit 33A generates feature amount image data by using the slope as the corrected feature amount, and adopt dispersion of the corrected feature amount c when the image processing unit 33A generates feature amount image data by using the mid-band fit as the corrected feature amount. This is because Equation (1) that gives the attenuation amount A(f, z) remains only ideal, and in reality, Equation (6) below is more appropriate.

$$A(f,z)=2\alpha z f+2\alpha_1 z \quad (6)$$

In Equation (6), $\alpha_1$ in the second term on the right side is a coefficient that represents a magnitude of a signal intensity change proportional to the reception depth z of the ultrasound wave, and is a coefficient that represents a signal intensity change that occurs when an observation target tissue is not uniform or the number of channels at the time of beam synthesis is changed. Due to the presence of the second term on the right side of Equation (6), when the feature amount image data is generated by using the mid-band fit as the corrected feature amount, it is more appropriate to set the optimal attenuation rate by using the dispersion of the corrected feature amount c in order to accurately correct attenuation (see Equation (4)). In contrast, when the feature amount image data is generated by using the slope that is a coefficient proportional to the frequency f, it is more appropriate to set the optimal attenuation rate by using the dispersion of the corrected feature amount a in order to accurately correct attenuation while eliminating the influence of the second item on the right side. For example, when the unit of the attenuation rate α is dB/cm/MHz, the unit of the coefficient $\alpha_1$ is dB/cm.

Here, the reason why it is possible to set the optimal attenuation rate based on the statistical variation is described. If the optimal attenuation rate is applied to the observation target, the feature amount converges to a value specific to the observation target and the statistical variation is reduced regardless of a distance between the observation target and the ultrasound transducer 21. In contrast, if an attenuation rate candidate value that is not appropriate for the observation target is adopted as the optimal attenuation rate, the attenuation correction may be excessively or insufficiently performed, so that the feature amount may deviate depending on the distance to the ultrasound transducer 21 and the statistical variation of the feature data may increase. Therefore, it is reasonable to conclude that the attenuation rate candidate value with the smallest statistical variation is the optimal attenuation rate for the observation object.

The image processing unit 33A includes a B-mode image data generation unit 331 that generates a B-mode image data that is an ultrasound image in which the amplitude of an echo signal is converted to and displayed as luminance, and a feature amount image data generation unit 332 that generates feature amount image data that is displayed together with the B-mode image by associating the feature amount calculated by the feature amount calculation unit 413 with visual information.

The B-mode image data generation unit 331 generates B-mode image data by performing signal processing using known technique, such as gain processing or contrast processing, on the B-mode reception data received from the signal processing unit 32, data thinning corresponding to a data step width that is determined depending on an image display range of the display device 4, or the like. The B-mode image is a grayscale image in which R (red), G (green), and B (blue) values are set to the same value when the RGB color system is adopted as the color system.

The B-mode image data generation unit 331 performs coordinate transformation on pieces of B-mode reception data received from the signal processing unit 32 for rearranging the piece of B-mode reception data so that a scanning range can be represented in a spatially correct manner, and performs an interpolation process between the pieces of B-mode reception data to fill gaps between the pieces of B-mode reception data, to thereby generate the B-mode image data. The B-mode image data generation unit 331 outputs the generated B-mode image data to the feature amount image data generation unit 332.

The feature amount image data generation unit 332 generates feature amount image data by superimposing visual information related to the feature amount calculated by the feature amount calculation unit 413 on each of pixels of an image of the B-mode image data. The feature amount image data generation unit 332 assigns, with respect to a pixel region corresponding to a data amount of the single sample data group $F_j$ (j=1, 2, . . . , K) illustrated in FIG. 17 for example, visual information corresponding to a feature amount of a frequency spectrum that is calculated from the sample data group $F_j$. The feature amount image data generation unit 332 generates the feature amount image data by associating, as the visual information, hue with any one of the slope, the intercept, and the mid-band fit as described above, for example. Meanwhile, the feature amount image data generation unit 332 may generate the feature amount image data by associating hue with one of two feature amounts selected from among the slope, the intercept, and the mid-band fit and associating tone with the other one of the two feature amounts. Examples of the visual information related to the feature amount include hue, saturation, brightness, a luminance value, a variable in a color space constituting a predetermined color system, such as R (red), G (green), B (blue).

Figure 20:
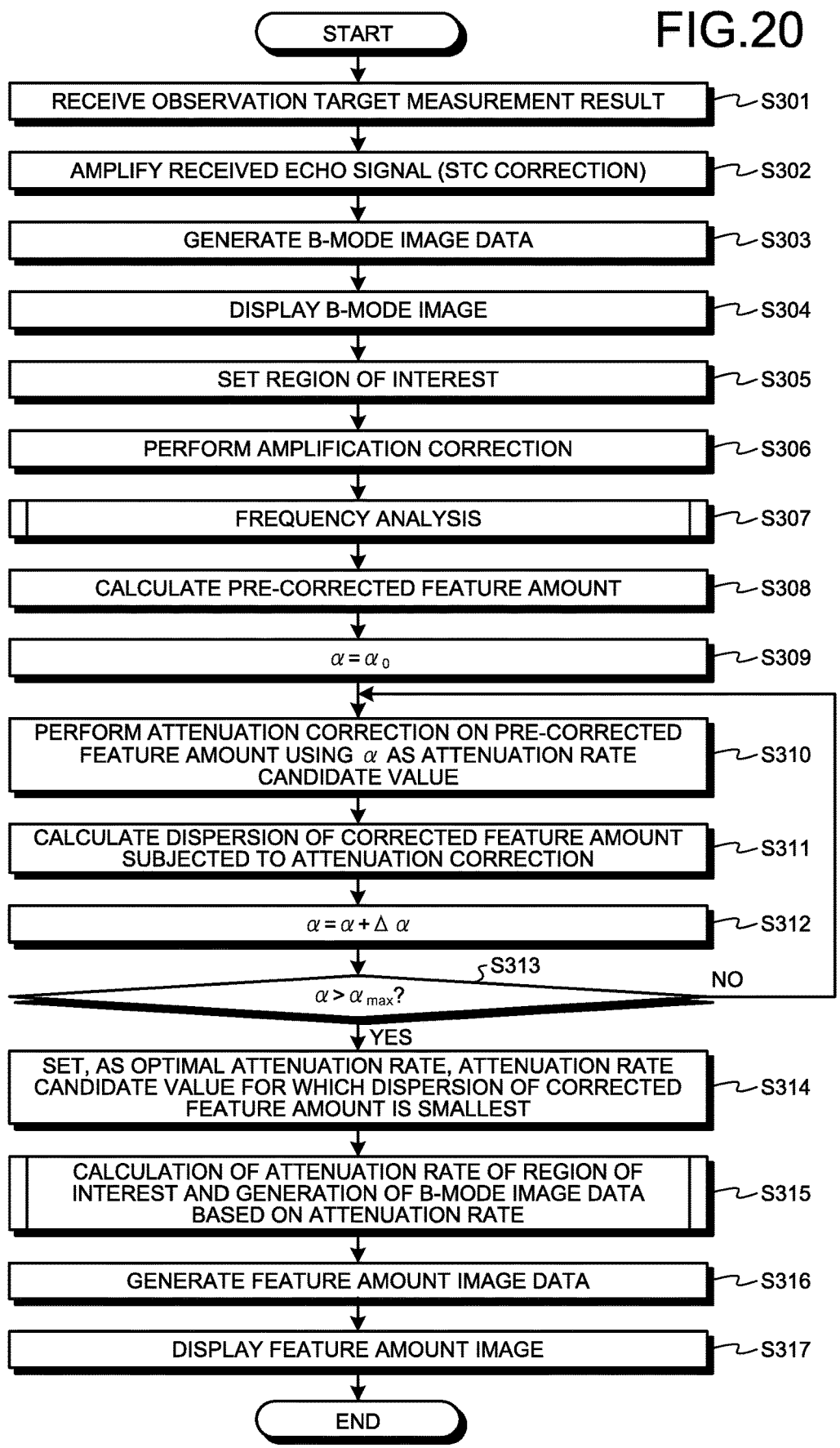
FIG. 20 is a flowchart illustrating the outline of a process performed by the ultrasound observation device according to the fifth embodiment.

FIG. 20 is a flowchart illustrating the outline of a process performed by the ultrasound observation device 3C configured as described above. First, the ultrasound observation device 3C receives, from the ultrasound endoscope 2, an echo signal that is an observation target measurement result obtained by the ultrasound transducer 21 (Step S301).

The signal amplification unit 311 that has received the echo signal from the ultrasound transducer 21 amplifies the echo signal (Step S302). Here, the signal amplification unit 311 performs amplification (STC correction) on the echo signal based on the relationship between the amplification factor and the reception depth as illustrated in FIG. 15, for example.

Subsequently, the B-mode image data generation unit 331 generates B-mode image data by using the echo signal amplified by the signal amplification unit 311, and outputs the B-mode image data to the display device 4 (Step S303). The display device 4 that has received the B-mode image data displays a B-mode image corresponding to the B-mode image data (Step S304).

At Step S305 following Step S304, the region-of-interest setting unit 36 sets a region of interest in accordance with a preset setting condition or a region-of-interest setting instruction received by the input unit 38.

The amplification correction unit 411 performs amplification correction on a signal output from the transmission/reception unit 31 such that the amplification factor becomes uniform regardless of the reception depth (Step S306). Here, the amplification correction unit 411 performs the amplification correction so that the relationship between the amplification factor and the reception depth as illustrated in FIG. 16 is established, for example.

Figure 21:
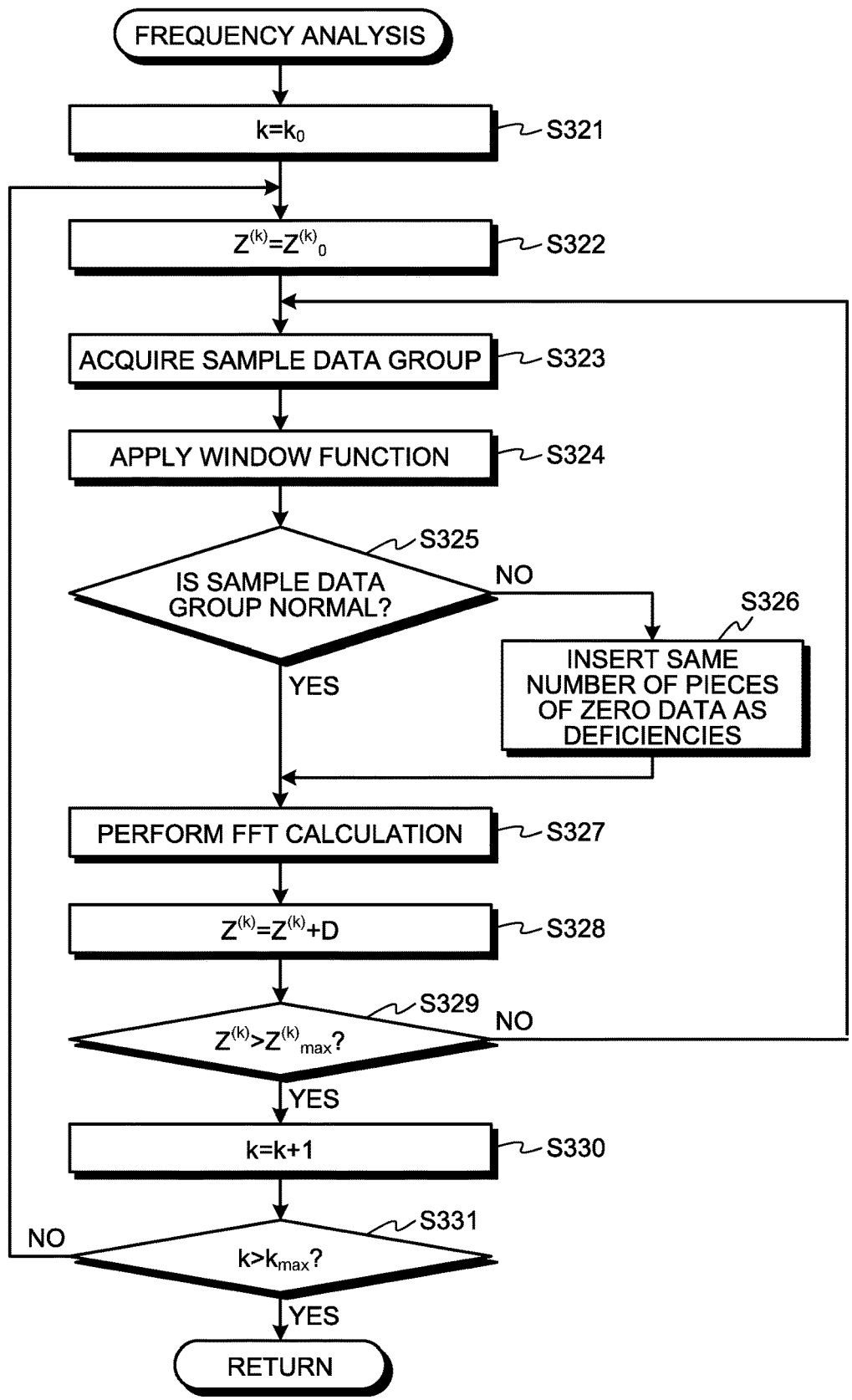
FIG. 21 is a flowchart illustrating the outline of a process performed by the frequency analysis unit of the ultrasound observation device according to the fifth embodiment.

Thereafter, the frequency analysis unit 412 calculates frequency spectrums for all of sample data groups by performing frequency analysis through an FFT calculation (Step S307). FIG. 21 is a flowchart illustrating the outline of a process performed by the frequency analysis unit 412 at Step S307. The frequency analysis process will be described in detail below with reference to the flowchart illustrated in FIG. 21.

First, the frequency analysis unit 412 sets a counter k for identifying a sound ray to be analyzed to $k_0$ (Step S321).

Subsequently, the frequency analysis unit 412 sets an initial value $Z^{(k)}{}_0$ of a data position (corresponding to the reception depth) $Z^{(k)}$ that represents a group of pieces of sequential data (sample data group) that is acquired for the FFT calculation (Step S322). For example, FIG. 17 illustrates a case in which the eighth data position of the sound ray $SR_k$ is set as the initial value $Z^{(k)}{}_0$ as described above.

Thereafter, the frequency analysis unit 412 acquires a sample data group (Step S323), and applies a window function stored in the storage unit 39 to the acquired sample data group (Step S324). By applying the window function to the sample data group as described above, it is possible to prevent sample data groups from being discontinued at boundaries and prevent occurrence of artifact.

Subsequently, the frequency analysis unit 412 determines whether the sample data group with the data position $Z^{(k)}$ is a normal data group (Step S325). As described above with reference to FIG. 17, the sample data group needs to have the same number of pieces of data as a power of two. Hereinafter, the number of pieces of data of a normal sample data group is represented by $2^n$ (n is a positive integer). In the fifth embodiment, the data position $Z^{(k)}$ is set so that the data position can be best possibly located at the center of the sample data group to which $Z^{(k)}$ belongs. Specifically, because the number of pieces of data in the sample data group is $2^n$, $Z^{(k)}$ is set to the $2^n/2(=2^{n-1})$-th position that is close to the center of the subject sample data group. In this case, a case in which the sample data group is normal indicates that $2^{n-1}-1$ (=N) pieces of data are present prior to the data position $Z^{(k)}$ and $2^{n-1}$ (=M) pieces of data are present posterior to the data position $Z^{(k)}$. In the example illustrated in FIG. 17, all of the sample data groups $F_1, F_2, F_3, \ldots, F_{k-1}$ are normal. Meanwhile, FIG. 17 illustrates a case in which n=4 (N=7 and M=8).

As a result of the determination at Step S325, if the sample data group with the data position $Z^{(k)}$ is normal (Step S325: Yes), the frequency analysis unit 412 proceeds to Step S327 to be described later.

As a result of the determination at Step S325, if the sample data group with the data position $Z^{(k)}$ is not normal (Step S325: No), the frequency analysis unit 412 generates a normal sample data group by inserting the same number of pieces of zero data as pieces of deficient data (Step S326). The sample data group that is determined as not being normal at Step S325 (for example, the sample data group $F_K$ in FIG. 17) is subjected to application of the window function before the zero data is added. Therefore, even when the zero data is inserted in the sample data group, data discontinuity does not occur. After Step S326, the frequency analysis unit 412 proceeds to Step S327 to be described below.

At Step S327, the frequency analysis unit 412 obtains a frequency spectrum that is a frequency distribution with respect to the amplitude, by performing the FFT calculation using the sample data group (Step S327).

Subsequently, the frequency analysis unit 412 changes the data position $Z^{(k)}$ by a step width D (Step S328). It is assumed that the step width D is stored in the storage unit 39 in advance. FIG. 17 illustrates an example in which D=15. It is desirable to set the step width D to the same data step width that is used when the B-mode image data generation unit 331 generates the B-mode image data; however, to reduce a calculation amount in the frequency analysis unit 412, it may be possible to set the step width D to a larger width than the data step width.

Thereafter, the frequency analysis unit 412 determines whether the data position $Z^{(k)}$ is larger than a maximum value $Z^{(k)}{}_{max}$ in the sound ray $SR_k$ (Step S329). If the data position $Z^{(k)}$ is larger than the maximum value $Z^{(k)}{}_{max}$ (Step S329: Yes), the frequency analysis unit 412 increments the counter k by one (Step S330). This means that the process is shifted to an adjacent sound ray. In contrast, if the data position $Z^{(k)}$ is equal to or smaller than the maximum value $Z^{(k)}{}_{max}$ (Step S329: No), the frequency analysis unit 412 returns to Step S323. In this manner, the frequency analysis unit 412 performs the FFT calculation on the same number of sample data groups as $[(Z^{(k)}{}_{max}-Z^{(k)}{}_0+1)/D+1]$ with respect to the sound ray $SR_k$. Here, [X] represents a maximum integer smaller than X.

After Step S330, the frequency analysis unit 412 determines whether the counter k is larger than the maximum value $k_{max}$ (Step S331). If the counter k is larger than the maximum value $k_{max}$ (Step S331: Yes), the frequency analysis unit 412 terminates a series of frequency analysis processes. In contrast, if the counter k is equal to or smaller than the maximum value $k_{max}$ (Step S331: No), the frequency analysis unit 412 returns to Step S322. It is assumed that the maximum value $k_{max}$ is a value that is arbitrarily designated and input by a user, such as an operator, via the input unit 38 or a value that is set in advance in the storage unit 39.

In this manner, the frequency analysis unit 412 performs the FFT calculation multiple times for each of $(k_{max}-k_0+1)$ sound rays in an analysis target region. A result of the FFT calculation is stored in the storage unit 39 together with a reception depth and a reception direction.

Following the frequency analysis process at Step S307 as described above, the feature amount calculation unit 413 calculates a pre-corrected feature amount of each of the frequency spectrums, calculates a corrected feature amount of each of the frequency spectrums by performing the attenuation correction of eliminating the influence of attenuation of ultrasound waves from the pre-corrected feature amount of each of the frequency spectrums with respect to each of the attenuation rate candidate values that give different attenuation properties when the ultrasound waves propagate through the observation target, and sets an optimal attenuation rate for the observation target from among the attenuation rate candidate values by using the corrected feature amount (Step S308 to S314). The processes from Steps S308 to S314 will be described in detail below.

At Step S308, the approximation unit 413a calculates the pre-corrected feature amount corresponding to each of the frequency spectrums by performing regression analysis on each of the frequency spectrums calculated by the frequency analysis unit 412 (Step S308). Specifically, the approximation unit 413a approximates each of the frequency spectrums by a linear expression by performing the regression analysis, and calculates the slope $a_0$, the intercept $b_0$, and the mid-band fit $c_0$ as the pre-corrected feature amounts. For example, the line $L_{10}$ illustrated in FIG. 18 is a regression line that is obtained by the approximation unit 413a by performing regression analysis on the frequency spectrum $C_1$ in the frequency band F.

At Step S309, the optimal attenuation rate setting unit 413c sets a value of an attenuation rate candidate value α, which is to be applied when attenuation correction (to be described later) is performed, to a predetermined initial value $α_0$. It is sufficient to store the value of the initial value $α_0$ in advance in the storage unit 39 and cause the optimal attenuation rate setting unit 413c to refer to the storage unit 39.

Subsequently, the attenuation correction unit 413b calculates a corrected feature amount by performing attenuation correction on the pre-corrected feature amount, which is obtained by the approximation unit 413a by approximating each of the frequency spectrums, by using a as an attenuation rate candidate value, and stores the corrected feature amount together with the attenuation rate candidate value α in the storage unit 39 (Step S310).

At Step S310, the attenuation correction unit 413b performs the calculation by assigning the data position $Z=(f_{sp}/2v_s)Dn$, which is obtained by using a data array of a sound ray of an ultrasound signal, to the reception depth z in Equations (2) and (4) as described above. Here, $f_{sp}$ is a data sampling frequency, $v_s$ is a sound speed, D is the data step width, n is the number of data steps from the first data of the sound ray to a data position of a processing target amplitude data group. For example, if the data sampling frequency $f_{sp}$ is set to 50 MHz, the sound speed $v_s$ is set to 1530 m/sec, and the step width D is set to 15 by adopting the data array illustrated in FIG. 17, Z=0.2295n (mm).

The optimal attenuation rate setting unit 413c calculates dispersion of a representative corrected feature amount among the plurality of corrected feature amounts that are obtained by the attenuation correction unit 413b by performing the attenuation correction on each of the frequency spectrums, and stores the representative corrected feature amount in association with the attenuation rate candidate value α in the storage unit 39 (Step S311). If the corrected feature amounts are the slope a and the mid-band fit c, the optimal attenuation rate setting unit 413c calculates, for example, dispersion of the corrected feature amount c. At Step S311, it is preferable for the optimal attenuation rate setting unit 413c to adopt the dispersion of the corrected feature amount a when the feature amount image data generation unit 332 generates feature amount image data by using the slope, and adopt the dispersion of the corrected feature amount c when the feature amount image data generation unit 332 generates feature amount image data by using the mid-band fit.

Thereafter, the optimal attenuation rate setting unit 413c increases the value of the attenuation rate candidate value α by Δα (Step S312), and compares a magnitude of the increased attenuation rate candidate value α and a magnitude of the predetermined maximum value $α_{max}$ (Step S313). As a result of the comparison at Step S313, if the attenuation rate candidate value α is larger than the maximum value $α_{max}$ (Step S313: Yes), the ultrasound observation device 3C proceeds to Step S314. In contrast, as a result of the comparison at Step S313, if the attenuation rate candidate value α is equal to or smaller than the maximum value $α_{max}$ (Step S313: No), the ultrasound observation device 3C returns to Step S310.

At Step S314, the optimal attenuation rate setting unit 413c refers to the dispersion for each of the attenuation rate candidate values stored in the storage unit 39, and sets an attenuation rate candidate value with the smallest dispersion as an optimal attenuation rate (Step S314).

When the optimal attenuation rate at each of the data positions is set, the ultrasound observation device 3C calculates an attenuation rate of the small region or the divided region set in the region of interest by using the attenuation rate as a physical quantity, and generates B-mode image data based on the attenuation rate (Step S315). Specifically, the ultrasound observation device 3C performs the processes from Steps S105 to S115 in the flowchart illustrated in FIG. 8, for example. For example, the determination unit 35 generates a histogram of the corrected feature amount c for each of the regions in the region of interest by using the corrected feature amount c as the physical quantity and determines whether a target region is uniform, and, the region change unit 362 and the calculation region setting unit 363 sets a region based on a determination result. Thereafter, the attenuation rate setting unit 37 sets an attenuation rate of each of the regions, and the B-mode image data generation unit 331 generates B-mode image data that is subjected to the attenuation correction with the set attenuation rate.

Thereafter, the feature amount image data generation unit 332 superimposes visual information (for example, hue) associated with the corrected feature amount that is calculated at Step S310 on each of pixels of the B-mode image data that is generated by the B-mode image data generation unit 331 at Step S315, and generates feature amount image data by adding information on the optimal attenuation rate (Step S316).

Figure 22:
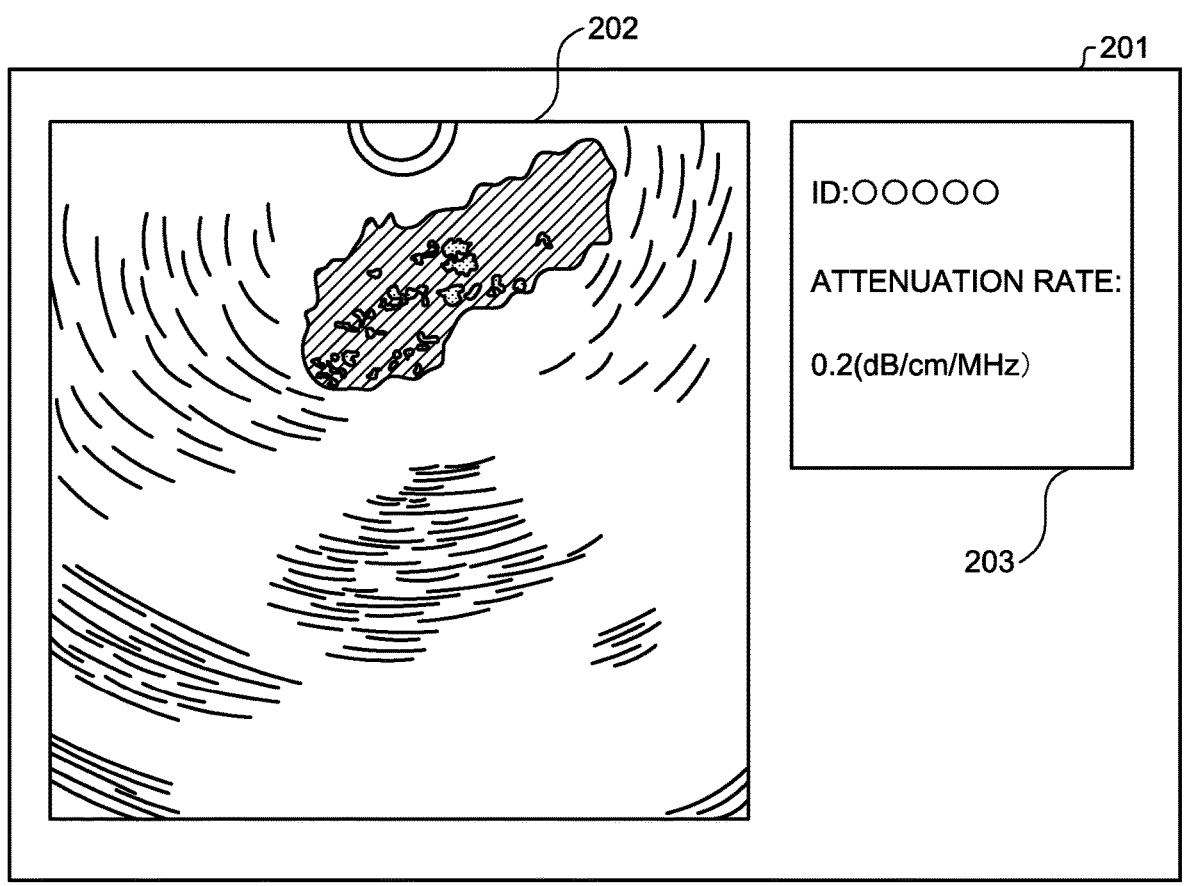
FIG. 22 is a diagram schematically illustrating a display example of a feature amount image on a display device of the ultrasound observation device according to the fifth embodiment.

At Step S317 following Step S316, the display device 4 displays a feature amount image corresponding to the feature amount image data generated by the feature amount image data generation unit 332 under the control of the control unit 40. FIG. 22 is a diagram schematically illustrating a display example of the feature amount image on the display device 4. A feature amount image 201 illustrated in FIG. 22 includes a superimposed image display portion 202 for displaying an image in which the visual information related to the feature amount is superimposed on the B-mode image, and an information display portion 203 for displaying identification information on an observation target or the like. Meanwhile, it may be possible to display, in the information display portion 203, information on the feature amount, information on the attenuation rate, information on an approximation formula, image information on gain and contrast, and the like. Further, it may be possible to display the B-mode image corresponding to the feature amount image side by side with the feature amount image.

According to the fifth embodiment as described above, the attenuation rate that is calculated through the frequency analysis is adopted as a physical quantity, whether the physical quantity is uniform is determined for each of regions set in a region of interest, the regions are divided in accordance with a determination result, and an attenuation rate is set in a region in which the physical quantity is uniform. Therefore, it is possible to maintain the size of the region of interest and appropriately set the attenuation rate in the region of interest. With use of the attenuation rate that is set as described above, it is possible to generate an ultrasound image with high accuracy.

Furthermore, according to the fifth embodiment, an optimal attenuation rate for an observation target is set from among a plurality of attenuation rate candidate values that give different attenuation properties when ultrasound waves propagate through the observation target, and a feature amount is calculated for each of frequency spectrums by performing attenuation correction by using the optimal attenuation rate. Therefore, it is possible to obtain an ultrasound wave attenuation property appropriate for the observation target by a simple calculation, and it is also possible to perform observation using the attenuation property.

Moreover, according to the fifth embodiment, the optimal attenuation rate is set based on a statistical variation of the corrected feature amount that is obtained by performing attenuation correction on each of the frequency spectrums. Therefore, it is possible to reduce a calculation amount as compared to the conventional technique in which fitting with a plurality of attenuation models is performed.

Meanwhile, in the fifth embodiment as described above, the optimal attenuation rate setting unit 413c may set, as the optimal attenuation rate, a cumulative attenuation rate that is obtained by cumulating attenuation rates until target data along a depth direction corresponding to the reception depth.

First Modification of Fifth Embodiment

Figure 23:
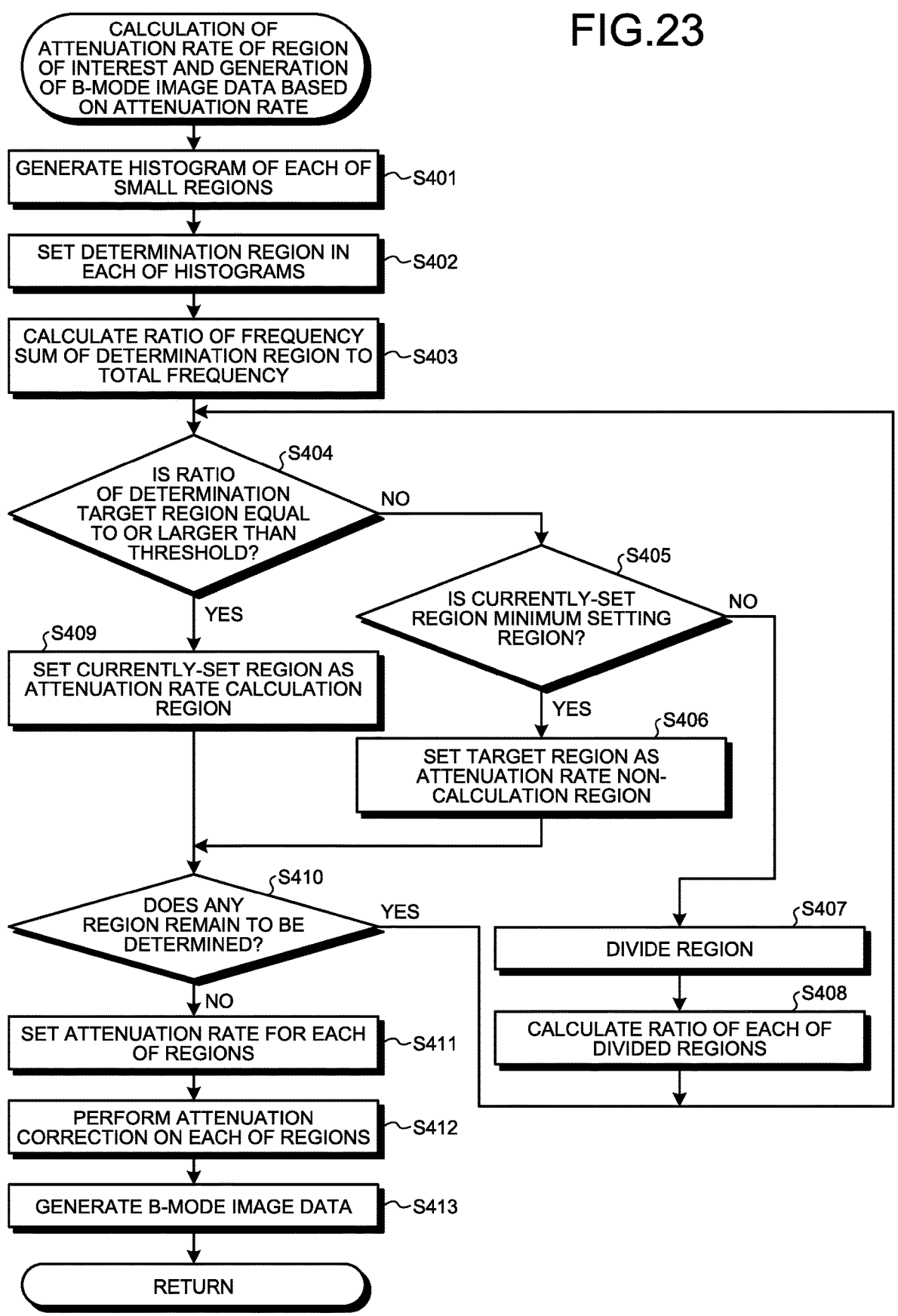
FIG. 23 is a flowchart illustrating the outline of a process performed by an ultrasound observation device according to a first modification of the fifth embodiment.

A first modification of the fifth embodiment will be described. FIG. 23 is a flowchart illustrating the outline of a process performed by an ultrasound observation device according to the first modification of the fifth embodiment. An ultrasound diagnosis system according to the first modification is the same as the ultrasound diagnosis system 1C as described above. Further, in the first modification, processes until display of a feature amount image are performed in the same manner as in FIG. 20 except that processing details at Step S315 in FIG. 20 are different. In the following, processes different from the fifth embodiment (calculation of an attenuation rate of a region of interest and generation of B-mode image data based on the attenuation rate) will be described.

At Step S401, the calculation unit 41 generates a histogram of a feature amount (for example, the corrected feature amount c) of each of the small regions with respect to a frequency ratio.

Figure 24:
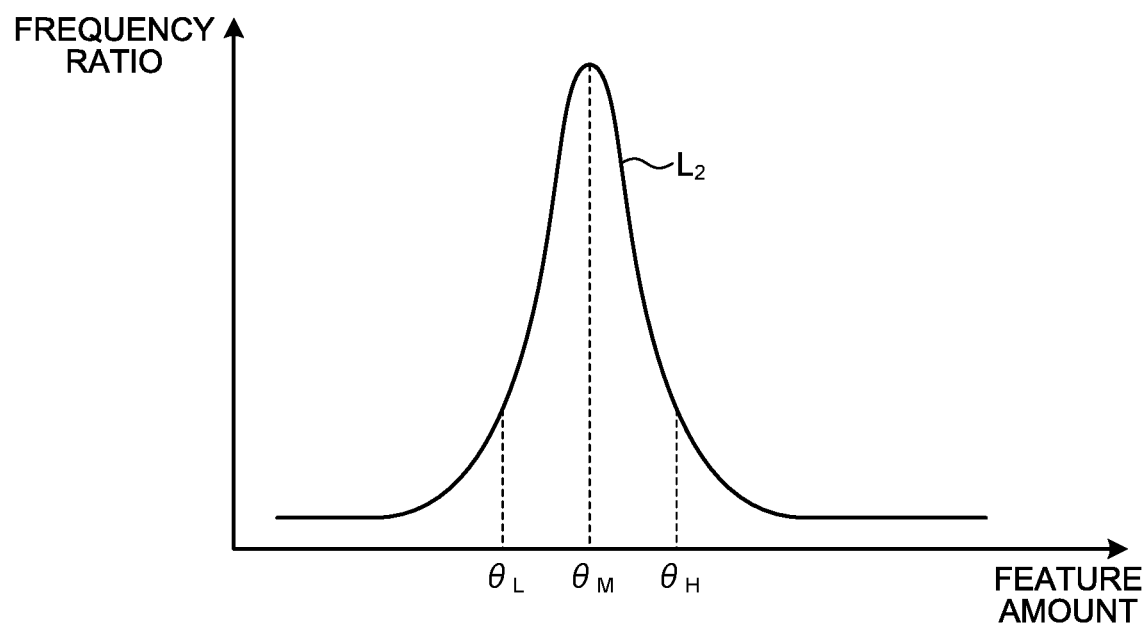
FIG. 24 is a diagram illustrating a frequency distribution of a frequency ratio with respect to a feature amount.
Figure 25:
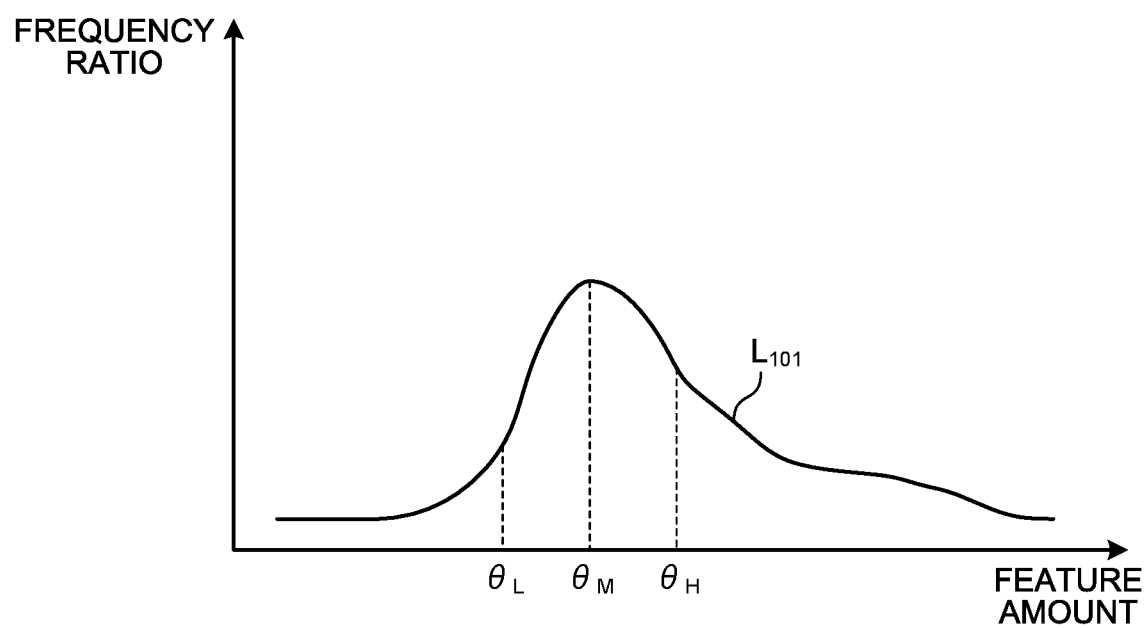
FIG. 25 is a diagram illustrating a frequency distribution of a frequency ratio with respect to a feature amount.

Thereafter, the calculation unit 41 sets a determination region centered at a feature amount corresponding to a peak of the histogram (Step S402). FIG. 24 and FIG. 25 are diagrams illustrating frequency distributions of a frequency ratio with respect to a feature amount. FIG. 24 and FIG. 25 illustrate curves $L_2$ and $L_{101}$ that are obtained by performing curve approximation on the histogram of the frequency ratio with respect to each feature amount. For example, as illustrated in FIGS. 24 and 25, the calculation unit 41 sets, as the determination region, a region centered at feature data $\theta_M$ corresponding to the peak of the histogram (in FIGS. 24 and 25, from feature data $\theta_L$ to feature data $\theta_H$). Meanwhile, a range of the determination region may be set to a different range for each of sites or may be set by each of users.

At Step S403 following Step S402, a ratio of a frequency sum of the determination region to a total frequency is calculated. Specifically, the calculation unit 41 calculates a sum (frequency sum) of frequencies of the set determination region and a total sum (total frequency) of all of frequencies. Thereafter, the calculation unit 41 calculates a ratio of the frequency sum to the total frequency. In the first modification, the corrected feature amount c is adopted as a physical quantity, and a ratio of the frequency sum calculated at Step S403 is adopted as a determination value.

At Step S404 following Step S403, the determination unit 35 compares the determination value (the ratio of the frequency sum) of the determination target region and a threshold stored in the storage unit 39, and determines whether the determination value is equal to or larger than the threshold. If the determination unit 35 determines that the determination value is smaller than the threshold (Step S404: No), the determination unit 35 determines that a target small region is not uniform (for example, see a curve $L_{101}$ illustrated in FIG. 25), and proceeds to Step S405. The threshold used at Step S403 is set based on, for example, past operation examples.

At Step S405, the region change unit 362 determines whether a size that is currently set for the determination target region corresponds to the minimum setting region. In this case, if the region change unit 362 determines that the determination target region is the minimum setting region (Step S405: Yes), the process proceeds to Step S406.

At Step S406, the region change unit 362 sets the target region as an attenuation rate non-calculation region and proceeds to Step S410.

In contrast, if the region change unit 362 determines that the determination target region is not the minimum setting region (Step S405: No), the process proceeds to Step S407.

At Step S407, the region change unit 362 further divides the target region similarly to Step S108. Thereafter, the calculation unit 41 calculates a determination value for each of the divided regions (Step S408). After the determination value is calculated, the control unit 40 returns to Step S404 and performs the determination process as described above.

In contrast, at Step S404, if the determination unit 35 determines that the determination value is equal to or larger than the threshold (Step S404: Yes), the determination unit 35 determines that the target small region is uniform (for example, see the curve $L_2$ illustrated in FIG. 24), and proceeds to Step S409.

At Step S409, the calculation region setting unit 363 sets the currently-set region as an attenuation rate calculation region. After the attenuation rate calculation region is set, the control unit 40 proceeds to Step S410.

At Step S410, the control unit 40 determines whether any region remains to be determined. If the control unit 40 determines that any region remains to be determined (Step S410: Yes), the control unit 40 returns to Step S404 and performs the above-described process on the region that remains to be determined. In contrast, if the control unit 40 determines that any region does not remain to be determined (Step S410: No), the process proceeds to Step S411.

At Step S411, the attenuation rate setting unit 37 sets an attenuation rate for each of the small regions and/or the divided regions that are set as the attenuation rate calculation regions. Thereafter, the signal processing unit 32 performs attenuation correction on each of the regions by using the set attenuation rate (Step S412).

The image processing unit 33A acquires B-mode reception data subjected to the attenuation correction, and generates B-mode image data including a B-mode image that is an ultrasound image (Step S413). After the B-mode image data is generated at Step S413, the control unit 40 returns to Step S316 and performs the above-described process.

In the first modification as described above, a frequency ratio that is calculated based on a feature amount is adopted as a physical quantity, whether the physical quantity is uniform is determined for each of regions set in a region of interest, the regions are divided in accordance with a determination result, and an attenuation rate is set in a region in which the physical quantity is uniform. Therefore, it is possible to maintain the size of the region of interest and appropriately set the attenuation rate in the region of interest. With use of the attenuation rate that is set as described above, it is possible to generate the ultrasound image with high accuracy.

Second Modification of Fifth Embodiment

Figure 26:
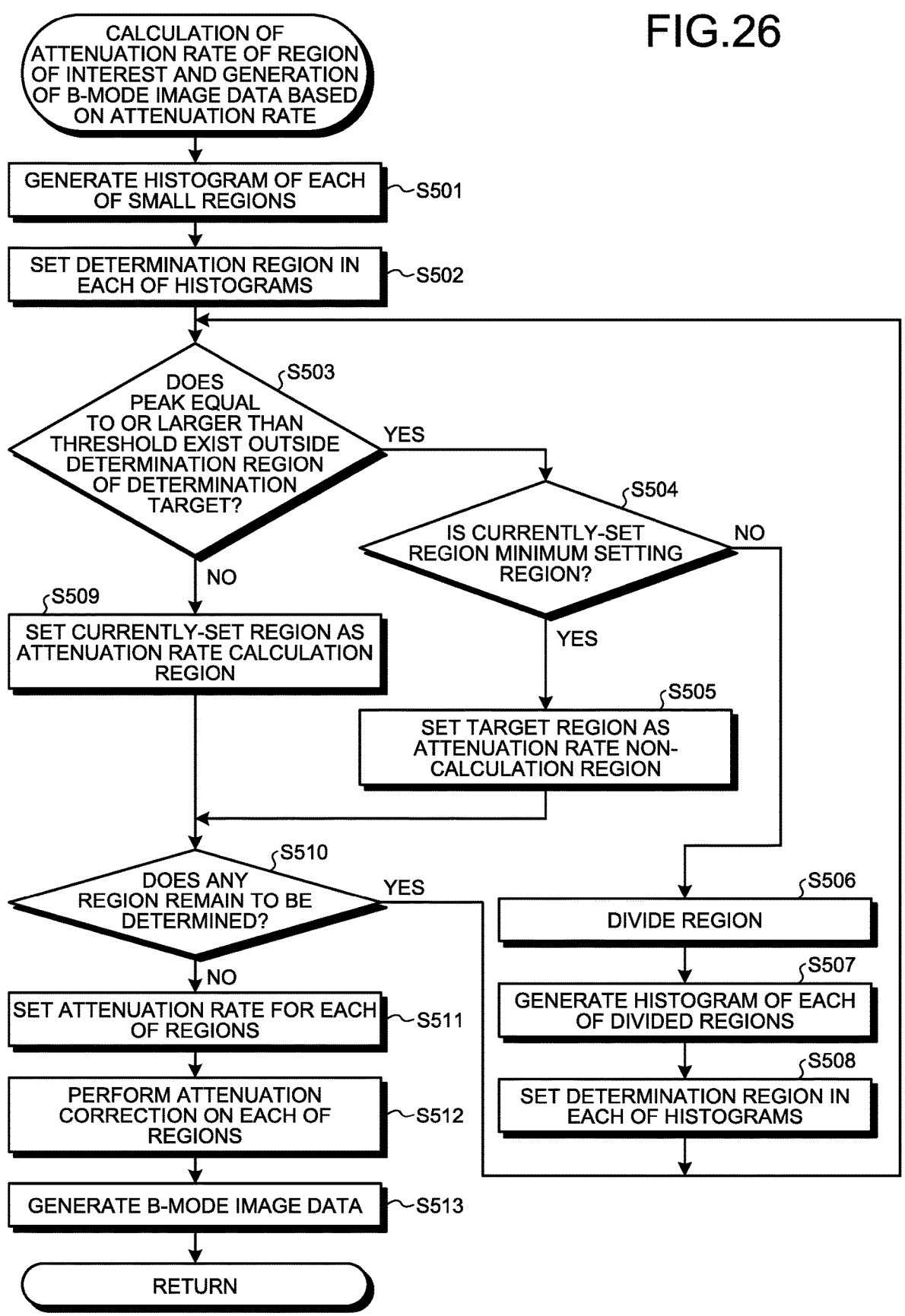
FIG. 26 is a flowchart illustrating the outline of a process performed by an ultrasound observation device according to a second modification of the fifth embodiment.

A second modification of the fifth embodiment will be described. FIG. 26 is a flowchart illustrating the outline of a process performed by an ultrasound observation device according to the second modification of the fifth embodiment. An ultrasound diagnosis system according to the second modification is the same as the ultrasound diagnosis system 1C as described above. Further, in the second modification, processes until display of a feature amount image are performed in the same manner as in FIG. 20 except that processing details at Step S315 in FIG. 20 are different. In the following, processes different from the fifth embodiment (calculation of an attenuation rate of a region of interest and generation of B-mode image data based on the attenuation rate) will be described.

At Step S501, the calculation unit 41 generates a histogram of a feature amount (for example, the corrected feature amount c) of each of the small regions with respect to a frequency ratio, similarly to Step S401 as described above.

Thereafter, the calculation unit 41 sets a determination region centered at a feature amount corresponding to a peak of the histogram (Step S502). In the second modification, a value of a frequency ratio (peak value) outside the determination region is adopted as a determination value.

At Step S503 following Step S502, if a peak exists outside the determination region, the determination unit 35 compares the peak value (determination value) and a threshold stored in the storage unit 39, and determines whether the determination value is equal to or larger than the threshold. If the determination unit 35 determines that the determination value is equal to or larger than the threshold (Step S503: Yes), the determination unit 35 determines that the target small region is not uniform and proceeds to Step S504. The threshold used at Step S503 is set based on, for example, past operation examples.

Figure 27:
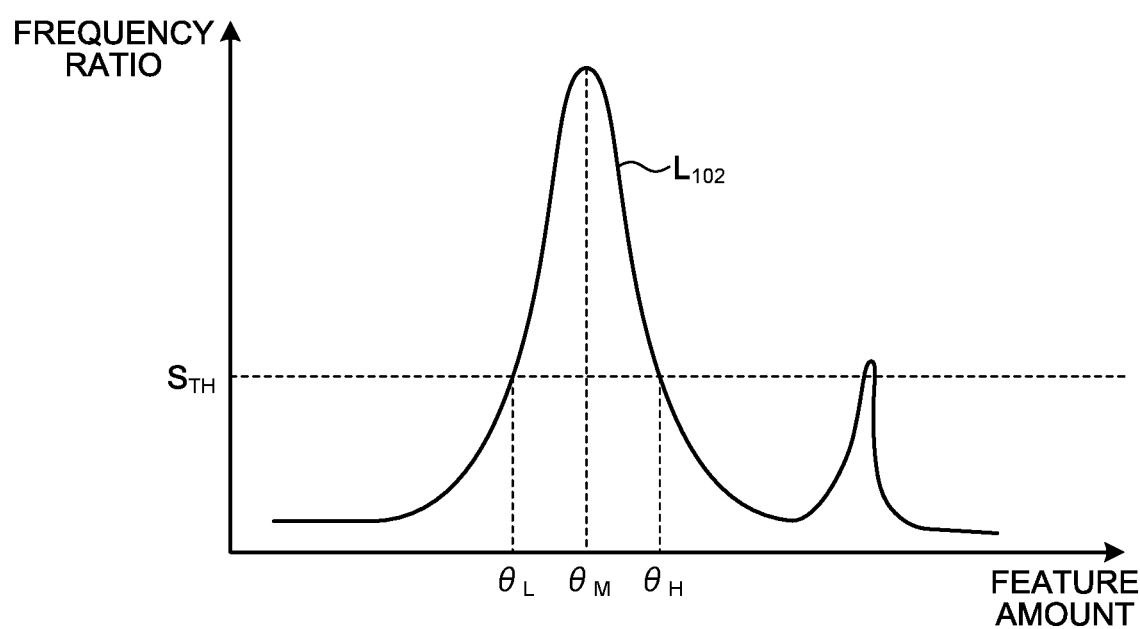
FIG. 27 is a diagram illustrating a frequency distribution of a frequency ratio with respect to a feature amount.

FIG. 27 is a diagram illustrating a frequency distribution of a frequency ratio with respect to a feature amount. FIG. 27 illustrates a curve $L_{102}$ that is obtained by performing curve approximation on the histogram of the frequency ratio with respect to each feature amount. The curve $L_{102}$ illustrated in FIG. 27 has a frequency-ratio peak larger than a frequency-ratio threshold $S_{TH}$ with respect to a feature amount that exists outside the region and that is larger than the feature amount $\theta_H$. In this case, the determination unit 35 determines that the target small region is not uniform.

At Step S505, the region change unit 362 determines whether a size that is currently set for the determination target region corresponds to the minimum setting region. In this case, if the region change unit 362 determines that the determination target region is the minimum setting region (Step S505: Yes), the process proceeds to Step S505.

At Step S505, the region change unit 362 sets the target region as an attenuation rate non-calculation region and proceeds to Step S510.

In contrast, if the region change unit 362 determines that the determination target region is not the minimum setting region (Step S504: No), the process proceeds to Step S506.

At Step S506, the region change unit 362 further divides the target region similarly to Step S108. Thereafter, the calculation unit 41 generates the above-described histogram for each of the divided regions (Step S507), and sets a determination region for the histogram (Step S508). After the determination region is set, the control unit 40 returns to Step S503 and performs the above-described determination process.

In contrast, at Step S504, if the determination unit 35 determines that the determination value (peak value) is smaller than the threshold or determines that a peak does not exist (Step S504: Yes), the determination unit 35 determines that the target small region is uniform (for example, see the curve $L_2$ illustrated in FIG. 24), and proceeds to Step S509. Meanwhile, if a peak does not exist outside the determination region, the determination unit 35 determines that the determination value is smaller than the threshold.

At Step S509, the calculation region setting unit 363 sets the currently-set region as an attenuation rate calculation region. After the attenuation rate calculation region is set, the control unit 40 proceeds to Step S510.

At Step S510, the control unit 40 determines whether any region remains to be determined. If the control unit 40 determines that any region remains to be determined (Step S510: Yes), the control unit 40 returns to Step S503 and performs the above-described process on the region that remains to be determined. In contrast, if the control unit 40 determines that any region does not remain to be determined (Step S510: No), the process proceeds to Step S511.

At Step S511, the attenuation rate setting unit 37 sets an attenuation rate for each of the small regions and/or the divided regions that are set as the attenuation rate calculation regions. Thereafter, the signal processing unit 32 performs attenuation correction on each of the regions by using the set attenuation rate (Step S512).

The image processing unit 33A acquires B-mode reception data subjected to the attenuation correction, and generates B-mode image data including a B-mode image that is an ultrasound image (Step S513). After the B-mode image data is generated at Step S513, the control unit 40 returns to Step S316 and performs the above-described process.

In the second modification as described above, a peak value of a frequency ratio that is calculated based on a feature amount and that exists outside a determination region is adopted as a physical quantity, whether the physical quantity is uniform is determined for each of regions set in the region of interest, the regions are divided in accordance with a determination result, and an attenuation rate is set in a region in which the physical quantity is uniform. Therefore, it is possible to maintain the size of the region of interest and appropriately set the attenuation rate in the region of interest. With use of the attenuation rate that is set as described above, it is possible to generate the ultrasound image with high accuracy.

Meanwhile, in the first and the second modifications of the fifth embodiment as described above, the examples have been described in which the corrected feature amount c is adopted as the physical quantity, but it may be possible to adopt luminance as the physical quantity as in the first to the fourth embodiments.

While the embodiments have been described above, the present disclosure is not limited to only the embodiments as described above. For example, while the examples have been described in which living tissue is adopted as an observation target, the technique may be applied to an industrial endoscope that observes properties of materials. The ultrasound observation device is applicable to both of inside and outside of body. Further, it may be possible to transmit and receive signals of the observation target by applying infrared or the like, instead of ultrasound waves.

Meanwhile, in the first to the fifth embodiments as described above, the examples have been described in which the determination unit 35 determines whether a target region is uniform by using, as a physical quantity, a corrected feature amount related to luminance of a B-mode image or a frequency feature amount, but the present disclosure is not limited thereto. Examples of the physical quantity include the corrected feature amount a related to the frequency feature amount, a spectral intensity, a value correlated to the spectral intensity, a value of change in elastography, and a sound speed.

While it is explained that the region-of-interest setting unit 36 includes the small region setting unit 361 and the region change unit 362 in the first to the fifth embodiments as described above, the region-of-interest setting unit 36, the small region setting unit 361, and the region change unit 362 may be independent of each other.

Furthermore, the ultrasound observation device may be configured such that circuits having various functions are connected via a bus or some functions are incorporated in circuit structures of other functions.

Moreover, while the embodiments have been described using the ultrasound endoscope that includes an optical system, such as a light guide, as an ultrasound probe, but the present disclosure is not limited to the ultrasound endoscope, and it may be possible to adopt an ultrasound probe that does not include an imaging optical system and an imaging element. Furthermore, as the ultrasound probe, it may be possible to adopt an ultrasound miniature probe that does not include an optical system and that has a small diameter. The ultrasound miniature probe is normally inserted in a biliary tract, a bile duct, a pancreatic duct, a trachea, a bronchus, a urethra, or a ureter, and used to observe surrounding organs (a pancreas, lungs, a prostate gland, a bladder, lymph nodes, or the like).

Furthermore, as the ultrasound probe, it may be possible to use an external ultrasound probe that applies ultrasound waves from a body surface of a subject. The external ultrasound probe is generally used to observe abdominal organs (a liver, a gallbladder, a bladder), a breast (in particular, a mammary gland), or a thyroid by being directly brought into contact with a body surface.

Moreover, the ultrasound transducer may be a linear transducer, a radial transducer, or a convex transducer. If the ultrasound transducer is a linear transducer, a scanning region is a rectangle (a rectangle or a square). If the ultrasound transducer is a radial transducer or a convex transducer, the scanning region is a sector shape or an annular shape.

As described above, the present disclosure include various embodiments within a scope that does not depart from a technical idea described in the appended claims.

As described above, the ultrasound observation device, the method of operating the ultrasound observation device, and a computer readable recording medium according to the present disclosure is useful to maintain the size of a region of interest and appropriately set an attenuation rate in the region of interest.

According to the present disclosure, it is possible to maintain the size of a region of interest and appropriately set an attenuation rate in the region of interest.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation device comprising:
  a processor comprising hardware, wherein the processor is configured to:
    set a region of interest in an ultrasound image;
    divide the region of interest into a plurality of first regions;
    calculate a variation of luminance for one first region of the plurality of first regions;
    compare the variation of luminance for the one first region to a predetermined threshold to determine whether the variation of luminance for the one first region is uniform;
    in response to determining that the variation of luminance for the one first region is not uniform, divide the one first region into a plurality of second regions; and
    set an attenuation rate of one second region of the plurality of second regions.

2. The ultrasound observation device according to claim 1,
  wherein, in response to determining that the variation of luminance for the one first region is uniform, set an attenuation rate of the one first region.

3. The ultrasound observation device according to claim 2,
  wherein the processor is configured to repeat dividing the region of interest into a plurality of first regions, calculating the variation of luminance for the one first region, and comparing the variation of luminance for the one first region to the predetermined threshold until the processor determines that the variation of luminance for the one first region is uniform or until sizes of the plurality of second regions reach a size of a preset minimum setting region.

4. The ultrasound observation device according to claim 3,
wherein, in response to determining that the variation of luminance for the one first region is not uniform, the processor is configured to:
determine whether the one first region is a minimum setting region;
in response to determining that the one first region is not the minimum setting region, divide the one first region into the plurality of the second regions; and
in response to determining that the one first region is the minimum setting region, set an attenuation rate of the one first region based on attenuation rates of other first regions of the plurality of the first regions adjacent to the one first region.

5. The ultrasound observation device according to claim 2,
wherein the processor is configured to:
in calculating the variation of the luminance for the one first region of the plurality of first regions, calculate a variation of a histogram of the luminance for the one first region of the plurality of the first regions; and
in comparing the variation of the luminance for the one first region to the predetermined threshold, compare the variation of the histogram of the luminance to the predetermined threshold to determine whether the variation of the luminance for the one first region is uniform.

6. The ultrasound observation device according to claim 2,
wherein the processor is configured to:
in calculating the variation of the luminance for the one first region of the plurality of first regions, calculate number of local maximum values of a histogram of the luminance for the one first region of the plurality of the first regions; and
in comparing the variation of the luminance for the one first region to the predetermined threshold, compare the number of the local maximum values to the predetermined threshold to determine whether the variation of the luminance for the one first region is uniform.

7. The ultrasound observation device according to claim 2,
wherein the processor is configured to:
in calculating the variation of the luminance for the one first region of the plurality of first regions,
calculate a histogram of the luminance for the one first region of the plurality of the first regions;
determine whether the histogram includes a plurality of local maximum values; and
in response to determining that the histogram includes a plurality of local maximum values, calculate a difference between luminance corresponding to the respective local maximum values; and
in comparing the variation of the luminance for the one first region to the predetermined threshold, compare the difference between the luminance corresponding to the respective local maximum values and the predetermined threshold to determine whether the variation of the luminance for the one first region is uniform.

8. A non-transitory computer-readable recording medium on which a program for operating an ultrasound observation device is recorded, the program instructing a processor to execute:
setting a region of interest in an ultrasound image;
dividing the region of interest into a plurality of first regions;
calculating a variation of luminance for one first region of the plurality of first regions;
comparing the variation of luminance for the one first region to a predetermined threshold to determine whether the variation of luminance for the one first region is uniform;
in response to determining that the variation of luminance for the one first region is not uniform, dividing the one first region into a plurality of second regions; and
setting an attenuation rate of one second region of the plurality of second regions.

9. The non-transitory computer-readable recording medium according to claim 8,
wherein the program instructs the processor to execute:
in response to determining that the variation of luminance for the one first region is uniform, setting an attenuation rate of the one first region.

10. The non-transitory computer-readable recording medium according to claim 9,
wherein the program instructs the processor to execute:
repeating dividing the region of interest into a plurality of first regions, calculating the variation of luminance for the one first region, and comparing the variation of luminance for the one first region to the predetermined threshold until the processor determines that the variation of luminance for the one first region is uniform or until sizes of the plurality of second regions reach a size of a preset minimum setting region.

11. The non-transitory computer-readable recording medium according to claim 10,
wherein the program instructs the processor to execute:
in response to determining that the variation of luminance for the one first region is not uniform:
determining whether the one first region is a minimum setting region;
in response to determining that the one first region is not the minimum setting region, dividing the one first region into the plurality of the second regions; and
in response to determining that the one first region is the minimum setting region, setting an attenuation rate of the one first region based on attenuation rates of other first regions of the plurality of the first regions adjacent to the one first region.

12. The non-transitory computer-readable recording medium according to claim 9,
wherein the program instructs the processor to execute:
in calculating the variation of the luminance for the one first region of the plurality of first regions, calculating a variation of a histogram of the luminance for the one first region of the plurality of the first regions; and
in comparing the variation of the luminance for the one first region to the predetermined threshold, comparing the variation of the histogram of the luminance to the predetermined threshold to determine whether the variation of the luminance for the one first region is uniform.

13. The non-transitory computer-readable recording medium according to claim 9,
wherein the program instructs the processor to execute:
in calculating the variation of the luminance for the one first region of the plurality of first regions, calculating number of local maximum values of a histogram of the luminance for the one first region of the plurality of the first regions; and
in comparing the variation of the luminance for the one first region to the predetermined threshold, comparing the number of the local maximum values to the predetermined threshold to determine whether the variation of the luminance for the one first region is uniform.

14. The non-transitory computer-readable recording medium according to claim 9,
wherein the program instructs the processor to execute:
in calculating the variation of the luminance for the one first region of the plurality of first regions,
calculating a histogram of the luminance for the one first region of the plurality of the first regions;
determining whether the histogram includes a plurality of local maximum values; and
in response to determining that the histogram includes a plurality of local maximum values, calculating a difference between luminance corresponding to the respective local maximum values; and
in comparing the variation of the luminance for the one first region to the predetermined threshold, comparing the difference between the luminance corresponding to the respective local maximum values and the predetermined threshold to determine whether the variation of the luminance for the one first region is uniform.

15. An ultrasound observation device comprising:
a processor comprising hardware, wherein the processor is configured to:
set a region of interest in an ultrasound image;
divide the region of interest into a plurality of first regions;
calculate a variation of luminance for one first region of the plurality of first regions;
compare the variation of luminance for the one first region to a predetermined threshold to determine whether the variation of luminance for the one first region is uniform;
in response to determining that the variation of luminance for the one first region is not uniform, divide the one first region into a plurality of second regions; and
in response to determining that the variation of luminance for the one first region is uniform, set an attenuation rate of the one first region.

16. The ultrasound observation device according to claim 15,
wherein the processor is configured to repeat dividing the region of interest into a plurality of first regions, calculating the variation of luminance for the one first region, and comparing the variation of luminance for the one first region to the predetermined threshold until the processor determines that the variation of luminance for the one first region is uniform or until sizes of the plurality of second regions reach a size of a preset minimum setting region.

17. The ultrasound observation device according to claim 16,
wherein, in response to determining that the variation of luminance for the one first region is not uniform, the processor is configured to:
determine whether the one first region is a minimum setting region;
in response to determining that the one first region is not the minimum setting region, divide the one first region into the plurality of the second regions; and
in response to determining that the one first region is the minimum setting region, set an attenuation rate of the one first region based on attenuation rates of other first regions of the plurality of the first regions adjacent to the one first region.

18. The ultrasound observation device according to claim 15,
wherein the processor is configured to:
in calculating the variation of the luminance for the one first region of the plurality of first regions, calculate a variation of a histogram of the luminance for the one first region of the plurality of the first regions; and
in comparing the variation of the luminance for the one first region to the predetermined threshold, compare the variation of the histogram of the luminance to the predetermined threshold to determine whether the variation of the luminance for the one first region is uniform.

19. The ultrasound observation device according to claim 15,
wherein the processor is configured to:
in calculating the variation of the luminance for the one first region of the plurality of first regions, calculate number of local maximum values of a histogram of the luminance for the one first region of the plurality of the first regions; and
in comparing the variation of the luminance for the one first region to the predetermined threshold, compare the number of the local maximum values to the predetermined threshold to determine whether the variation of the luminance for the one first region is uniform.

20. The ultrasound observation device according to claim 15,
wherein the processor is configured to:
in calculating the variation of the luminance for the one first region of the plurality of first regions,
calculate a histogram of the luminance for the one first region of the plurality of the first regions;
determine whether the histogram includes a plurality of local maximum values; and
in response to determining that the histogram includes a plurality of local maximum values, calculate a difference between luminance corresponding to the respective local maximum values; and
in comparing the variation of the luminance for the one first region to the predetermined threshold, compare the difference between the luminance corresponding to the respective local maximum values and the predetermined threshold to determine whether the variation of the luminance for the one first region is uniform.

* * * * *